United States Patent
Roettger et al.

(10) Patent No.: US 11,661,388 B2
(45) Date of Patent: May 30, 2023

(54) PROCESS FOR THE ENERGY-EFFICIENT PRODUCTION OF ALKALI METAL ALKOXIDES

(71) Applicant: Evonik Functional Solutions GmbH, Niederkassel (DE)

(72) Inventors: Dirk Roettger, Cologne (DE); Sebastian Reimann, Wesseling (DE); Armin Matthias Rix, Marl (DE); Niklas Paul, Marl (DE); Moritz Schröder, Muenster (DE); Philip Zitzewitz, Haltern am See (DE)

(73) Assignee: Evonik Functional Solutions GmbH, Niederkassel (DE)

( * ) Notice: Subject to any disclaimer, the term of this patent is extended or adjusted under 35 U.S.C. 154(b) by 0 days.

(21) Appl. No.: 17/659,053

(22) Filed: Apr. 13, 2022

(65) Prior Publication Data
US 2022/0340508 A1 Oct. 27, 2022

(30) Foreign Application Priority Data
Apr. 16, 2021 (EP) .................................. 21168921

(51) Int. Cl.
*C07C 29/70* (2006.01)
*B01D 3/00* (2006.01)
(Continued)

(52) U.S. Cl.
CPC .............. *C07C 29/70* (2013.01); *B01D 3/007* (2013.01); *B01D 3/009* (2013.01); *B01D 3/143* (2013.01); *B01D 3/26* (2013.01); *B01D 3/322* (2013.01)

(58) Field of Classification Search
None
See application file for complete search history.

(56) References Cited

U.S. PATENT DOCUMENTS 1,910,331 A 5/1933 Halbig
2,877,274 A 3/1959 Kramis
(Continued)

FOREIGN PATENT DOCUMENTS

CN 109627145 4/2019
DE 968903 4/1958
(Continued)

OTHER PUBLICATIONS

CN109627145—machinetranslation—Apr. 16, 2019; pp. 1-9 (Year: 2019).*
(Continued)

*Primary Examiner* — Medhanit W Bahta
(74) *Attorney, Agent, or Firm* — Grüneberg and Myers, PLLC

(57) ABSTRACT

A process produces sodium and/or potassium alkoxides in countercurrent by reactive rectification. Alcohol is reacted in countercurrent with the respective alkali metal hydroxide. The vapours containing alcohol and water are separated into at least two serially arranged rectification columns. The energy of the vapour obtained in the first rectification is utilized for operating the second rectification. This specific
(Continued)

energy integration coupled with establishing a certain pressure difference in the two rectification stages makes it possible to cover a particularly large proportion of the energy required for the rectification through electricity and to save heating steam.

16 Claims, 4 Drawing Sheets

(51) Int. Cl.
*B01D 3/14* (2006.01)
*B01D 3/26* (2006.01)
*B01D 3/32* (2006.01)

(56) References Cited

U.S. PATENT DOCUMENTS

| | | |
|---|---|---|
| 4,566,947 A | 1/1986 | Tsuruta |
| 4,895,989 A | 1/1990 | Sander et al. |
| 7,847,133 B2 | 12/2010 | Ruwwe et al. |
| 2002/0183566 A1 | 12/2002 | Guth et al. |
| 2008/0296786 A1 | 12/2008 | Ruwwe et al. |
| 2010/0095703 A1 | 4/2010 | Jork et al. |
| 2011/0313207 A1 | 12/2011 | Kaibel et al. |
| 2012/0066965 A1 | 3/2012 | Ruwwe et al. |
| 2022/0340509 A1 | 10/2022 | Roettger et al. |
| 2023/0028559 A1* | 1/2023 | Roettger ................. C07C 29/70 |

FOREIGN PATENT DOCUMENTS

| | | |
|---|---|---|
| GB | 377631 | 7/1932 |
| GB | 737453 | 9/1955 |
| WO | 2010/097318 | 9/2010 |
| WO | 2021/148174 | 7/2021 |
| WO | 2021/148175 | 7/2021 |
| WO | 2022/161869 | 8/2022 |
| WO | 2022/167311 | 8/2022 |

OTHER PUBLICATIONS

U.S. Appl. No. 17/659,086, filed Apr. 13, 2022, 2022/0340509, Roettger et al.
U.S. Appl. No. 60/935,715, filed Aug. 28, 2007, Ruwwe et al.
U.S. Appl. No. 13/234,293, filed Sep. 16, 2011, 2012/0066965, Ruwwe et al.
Extended European Search Report dated Oct. 7, 2021 in European Patent Application No. 21168921.1, with English translation, 12 pages.
Ott et al., "Methanol", Ullmann's Encyclopedia of Industrial Chemistry, pp. 1-27.

\* cited by examiner

PROCESS FOR THE ENERGY-EFFICIENT PRODUCTION OF ALKALI METAL ALKOXIDES

CROSS-REFERENCE TO RELATED APPLICATIONS

This application claims priority to European Application No. 21168921.1, filed on Apr. 16, 2021, the content of which is hereby incorporated by reference in its entirety.

BACKGROUND OF THE INVENTION

Field of the Invention

The present invention relates to a process for producing sodium and/or potassium alkoxides in countercurrent by reactive rectification. Alcohol is reacted in countercurrent with the respective alkali metal hydroxide. The vapours comprising alcohol and water are separated into at least two serially arranged rectification columns. The energy of the vapours obtained in the first rectification is utilized for operating the second rectification. This specific energy integration coupled with establishing a certain pressure difference in the two rectification stages makes it possible to cover a particularly large proportion of the energy required for the rectification through electricity and to save heating steam.

Description of Related Art

The production of alkali metal alkoxides is an important industrial process.

Alkali metal alkoxides are used as strong bases in the synthesis of numerous chemicals, for example in the production of pharmaceutical or agrochemical active ingredients. Alkali metal alkoxides are also used as catalysts in transesterification and amidation reactions.

Alkali metal alkoxides (MOR) are produced by reactive distillation of alkali metal hydroxides (MOH) and alcohols (ROH) in a countercurrent distillation column, wherein the water of reaction formed according to the following reaction <1> is removed with the distillate.

$$MOH + ROH \rightleftharpoons MOR + H_2O.$$

Such a process principle by which aqueous alkali metal hydroxide solution and gaseous methanol are run in countercurrent in a rectification column is disclosed for example in U.S. Pat. No. 2,877,274 A. This process is described again in generally unchanged form in WO 01/42178 A1.

Similar processes, which additionally employ an entraining agent such as for example benzene, are disclosed in GB 377,631 A and U.S. Pat. No. 1,910,331 A. This entraining agent is used to separate water and the water-soluble alcohol. In both patents the condensate is subjected to a phase separation to separate off the water of reaction.

Correspondingly, DE 96 89 03 C describes a process for continuous production of alkali metal alkoxides in a reaction column, wherein the water-alcohol mixture withdrawn at the top of the column is condensed and then subjected to a phase separation. The aqueous phase is discarded and the alcoholic phase is returned to the top of the column together with the fresh alcohol. EP 0 299 577 A2 describes a similar process, wherein the water in the condensate is separated off with the aid of a membrane.

The most industrially important alkali metal alkoxides are those of sodium and potassium, especially the methoxides and ethoxides. Their synthesis is frequently described in the prior art, for example in EP 1 997 794 A1.

The syntheses or alkali metal alkoxides by reactive rectification described in the prior art typically afford vapours comprising the employed alcohol and water. It is advantageous for economic reasons to reuse the alcohol comprised in the vapours as a reactant in the reactive distillation. The vapours are therefore typically supplied to a rectification column and the alcohol present therein is separated off (described for example in GB 737 453 A and U.S. Pat. No. 4,586,947 A). The thus recovered alcohol is then supplied to the reactive distillation as a reactant for example. Alternatively or in addition a portion of the alcohol vapour may be utilized for heating the rectification column (described in WO 2010/097318 A1). However, this requires that the vapour be compressed in order to achieve the temperature level required for heating the rectification column. The vapour is cooled between the compression stages, wherein a multistage compression is thermodynamically advantageous and an Intermediate cooling ensures that the maximum allowable temperature of the compressor is not exceeded.

Heat integration within the rectification stage for efficient utilization of employed energy is described in a different context in Ott, J., Gronemann, V., Pontzen, F., Fiedler, E., Grossmann, G., Kersebohm, D. B., Weiss, G. and Witte, C. (2012). Methanol. In Ullmann's Encyclopedia of Industrial Chemistry, (Ed.). (doi:10.1002/14358007.a16_485.pub3). Paragraph 5.4 of this citation discloses the workup of crude methanol obtained in conventional synthesis processes by rectification using a plurality of rectification columns. It generally proposes utilizing the heat of condensation of the vapour obtained at the rectification column at relatively high pressure for heating the rectification column at relatively low pressure. However, this citation discloses nothing about advantageous energy integration in the separation of water-methanol vapours produced in the reactive rectification of alkali metal alkoxides.

In the production of alkali metal alkoxides it is possible on an industrial scale, particularly in integrated plants (chemistry parks, technology parks), to utilize heating steam as the energy source for covering the energy demand. Said steam is typically generated in excess in Integrated plants and may be utilized.

However, depending on infrastructure and available energy sources heating steam is not always available and in certain cases electricity is more cost-effective. In these cases there is a need for processes for producing alkali metal alkoxides where a lowest possible proportion of energy need be covered through heating steam and a highest possible proportion may be covered through electricity.

SUMMARY OF THE INVENTION

It is accordingly an object of the present invention to provide an improved process for production of alkoxides of sodium and potassium by reactive distillation. Said process shall especially allow energy-efficient utilization of the heat liberated during compression and cooling of the vapours. It should also cover a highest possible proportion of the energy requirements through electricity as an external energy source and feature a lowest possible heating steam demand.

The present invention accordingly provides a process for producing at least one alkali metal alkoxide of formula $M_A OR$, wherein R is a $C_1$ to $C_6$ hydrocarbon radical, preferably methyl or ethyl, and wherein $M_A$ is selected from sodium, potassium, and wherein $M_A$ is preferably sodium, wherein:

(a1) a reactant stream $S_{AE1}$ comprising ROH is reacted with a reactant stream $S_{AE2}$ comprising $M_AOH$ in countercurrent at a pressure $p_{3A}$ and a temperature $T_{3A}$ in a reactive rectification column $RR_A$ to afford a crude product $RP_A$ comprising $M_AOR$, water, ROH, $M_AOH$,
wherein a bottoms product stream $S_{AP}$ comprising ROH and $M_AOR$ is withdrawn at the lower end of $RR_A$ and a vapor stream $S_{AB}$ comprising water and ROH is withdrawn at the upper end of $RR_A$,
(a2) and optionally, simultaneously with and spatially separate from step (a1), a reactant stream $S_{BE1}$ comprising ROH is reacted with a reactant stream $S_{BE2}$ comprising $M_BOH$ in countercurrent at a pressure $p_{3B}$ and a temperature $T_{3B}$ in a reactive rectification column $RR_B$ to afford a crude product $RP_B$ comprising $M_BOR$, water, ROH, $M_BOH$, wherein $M_B$ is selected from sodium, potassium, and wherein $M_B$ is preferably potassium,
wherein a bottoms product stream $S_{BP}$ comprising ROH and $M_B$ OR is withdrawn at the lower end of $RR_B$ and a vapour stream $S_{BB}$ comprising water and ROH is withdrawn at the upper end of $RR_B$,
(b) the vapour stream $S_{AB}$ and if step (a2) is performed the vapour stream $S_{BB}$ in admixture with $S_{AB}$ or separately from $S_{AB}$ is passed into a first rectification column $RD_1$,
to obtain a mixture $G_{RD1}$ comprising water and ROH in the first rectification column $RD_1$,
(c) the mixture $G_{RD1}$ is in the first rectification column $RD_1$ at a pressure $p_1$ and a temperature $T_1$ separated into an ROH-comprising vapour stream $S_{RDB1}$ at the upper end of $RD_1$ and a bottoms stream $S_{RDS1}$ comprising water and ROH at the lower end of $RD_1$,
(d) the bottoms stream $S_{RDS1}$ is completely or partially passed into a second rectification column $RD_2$,
to obtain a mixture $G_{RD2}$ comprising water and ROH in the second rectification column $RD_2$,
(e) the mixture $G_{RD2}$ is at a pressure $p_2$ and a temperature $T_2$ separated into an ROH-comprising vapour stream $S_{RDB2}$ at the top of $RD_2$ and a bottoms stream $S_{RDS2}$ comprising water and optionally ROH at the lower end of $RD_2$,
characterized
in that $p_1 > p_2$, $p_1 > p_{3A}$ and in the cases in which step (a2) is performed $p_1 > p_{3B}$ and wherein preferably in addition $p_{3A} > p_2$ and in the cases in which step (a2) is performed preferably in addition furthermore $p_{3B} > p_2$
and in that (f) energy from $S_{RDB1}$ is transferred to the mixture $G_{RD2}$ in the second rectification column $RD_2$.

The invention also includes the following embodiments:
1. Process for producing at least one alkali metal alkoxide of formula $M_AOR$, wherein R is a $C_1$ to $C_6$ hydrocarbon radical and wherein $M_A$ is selected from sodium, potassium, wherein:
(a1) a reactant stream $S_{AE1}$ comprising ROH is reacted with a reactant stream $S_{AE2}$ comprising $M_AOH$ in countercurrent at a pressure $p_{3A}$ and a temperature $T_{3A}$ in a reactive rectification column $RR_A$ to afford a crude product $RP_A$ comprising $M_AOR$, water, ROH, $M_AOH$,
wherein a bottoms product stream $S_{AP}$ comprising ROH and $M_AOR$ is withdrawn at the lower end of $RR_A$ and a vapour stream $S_{AB}$ comprising water and ROH is withdrawn at the upper end of $RR_A$,
(a2) and optionally, simultaneously with and spatially separate from step (a1), a reactant stream $S_{BE1}$ comprising ROH is reacted with a reactant stream $S_{BE2}$ comprising $M_BOH$ in countercurrent at a pressure $p_{3B}$ and a temperature $T_{3B}$ in a reactive rectification column $RR_B$ to afford a crude product $RP_B$ comprising $M_BOR$, water, ROH, $M_BOH$, wherein $M_B$ is selected from sodium, potassium,
wherein a bottoms product stream $S_{BP}$ comprising ROH and $M_BOR$ is withdrawn at the lower end of $RR_B$ and a vapour stream $S_{BB}$ comprising water and ROH is withdrawn at the upper end of $RR_B$,
(b) the vapour stream $S_{AB}$ and if step (a2) is performed the vapour stream $S_{BB}$ in admixture with $S_{AB}$ or separately from $S_{AB}$ is passed into a first rectification column $RD_1$,
to obtain a mixture $G_{RD1}$ comprising water and ROH in the first rectification column $RD_1$,
(c) the mixture $G_{RD1}$ is in the first rectification column $RD_1$ at a pressure $p_1$ and a temperature $T_1$ separated into an ROH-comprising vapour stream $S_{RDB1}$ at the upper end of $RD_1$ and a bottoms stream $S_{RDS1}$ comprising water and ROH at the lower end of $RD_1$,
(d) the bottoms stream $S_{RDS1}$ is completely or partially passed into a second rectification column $RD_2$,
to obtain a mixture $G_{RD2}$ comprising water and ROH in the second rectification column $RD_2$,
(e) the mixture $G_{RD2}$ is at a pressure $p_2$ and a temperature $T_2$ separated into an ROH-comprising vapour stream $S_{RDB2}$ at the top of $RD_2$ and a bottoms stream $S_{RDS2}$ comprising water at the lower end of $RD_2$,
characterized in that
$p_1 > p_2$, $p_1 > p_{3A}$ and in the cases where step (a2) is performed $p_1 > p_{3B}$,
and in that (f) energy from $S_{RDB1}$ is transferred to the mixture $G_{RD2}$ in the second rectification column $RD_2$.
2. Process according to embodiment 1, wherein in step (f) energy is directly transferred from $S_{RDB1}$ to $G_{RD2}$.
3. Process according to embodiment 2, wherein at least one of the steps (α-i), (α-ii), (α-iii) is performed:
(α-i) energy from $S_{RDB1}$ is transferred to a portion $S_{RDS22}$ of the bottoms stream $S_{RDS2}$ discharged from $RD_2$ and $S_{RDS22}$ is then recycled into $RD_2$;
(α-ii) at least one stream $S_{RDX2}$ distinct from $S_{RDB2}$ and $S_{RDS2}$ comprising ROH and water is discharged from $RD_2$, energy is then transferred from $S_{RDB1}$ to $S_{RDX2}$ and $S_{RDX2}$ is recycled into $RD_2$;
(α-iii) $S_{RDB1}$ is passed through $RD_2$, thus transferring energy from $S_{RDB1}$ to $G_{RD2}$.
4. Process according to embodiment 1, wherein in step (f) energy is indirectly transferred from $S_{RDB1}$ to $G_{RD2}$.
5. Process according to embodiment 4, wherein at least one of the steps (β-i), (β-ii), (β-iii) is performed:
(β-i) a portion $S_{RDS22}$ of the bottoms stream $S_{RDS2}$ discharged from $RD_2$ is recycled into the second rectification column $RD_2$, wherein energy is transferred from $S_{RDB1}$ to at least one heat transfer medium $W_{i1}$ distinct from $S_{RDS22}$ and then transferred from the at least one heat transfer medium $W_{i1}$ to $S_{RDS22}$ and $S_{RDS22}$ is then recycled into $RD_2$;
(β-ii) at least one stream $S_{RDX2}$ distinct from $S_{RDB2}$ and $S_{RDS2}$ comprising ROH and water is discharged from $RD_2$ and energy is transferred from $S_{RDB1}$ to at least one heat transfer medium $W_{ii1}$ distinct from $S_{RDX2}$ and then transferred from the at least one heat transfer medium $W_{ii1}$ to $S_{RDX2}$ and $S_{RDX2}$ is then recycled into $RD_2$;
(β-iii) energy is transferred from $S_{RDB1}$ to at least one heat transfer medium $W_{iii1}$ distinct from $G_{RD2}$ and the at least one heat transfer medium $W_{iii1}$ is then passed through $RD_2$, thus transferring energy from the at least one heat transfer medium $W_{iii1}$ to $G_{RD2}$.
6. Process according to embodiment 5, wherein each of $W_{i1}$, $W_{ii1}$, $W_{iii1}$ is water.
7. Process according to any of embodiments 3, 5 and 6, wherein $S_{RDX2}$ is withdrawn below the vapour stream $S_{RDB2}$ on $RD_2$.

8. Process according to any of embodiments 1 to 7, wherein $S_{RDB2}$ is at least partially employed as reactant stream $S_{AE1}$ in the reactive rectification column $RR_A$ and if step (a2) is performed alternatively or in addition employed as reactant stream $S_{BE1}$ in the reactive rectification column $RR_B$.

9. Process according to any of embodiments 1 to 8, wherein $S_{RDB1}$ is at least partially employed as reactant stream $S_{AE1}$ in the reactive rectification column $RR_A$ and if step (a2) is performed alternatively or in addition employed as reactant stream $S_{BE1}$ in the reactive rectification column $RR_B$.

10. Process according to any of embodiments 1 to 9, wherein a stream $S_{XE1}$ distinct from $S_{AE1}$ and $S_{BE1}$ comprising ROH is added to at least one of the columns selected from rectification column $RD_1$, rectification column $RD_2$, reactive rectification column $RR_A$ and if step (a2) is performed is alternatively or in addition added to reactive rectification column $RR_B$.

11. Process according to any of embodiments 1 to 10, wherein R is methyl or ethyl.

12. Process according to any of embodiments 1 to 11, wherein step (a2) is performed.

13. Process according to any of embodiments 1 to 12, wherein $p_{3A} > p_2$ and in addition in cases where step (a2) is performed $p_{3B} > p_2$.

14. Process according to any of embodiments 1 to 13, wherein the bottoms stream $S_{RDS2}$ comprises water and ROH.

15. Process according to any of embodiments 1 to 14 which is carried out continuously.

Figure 1:
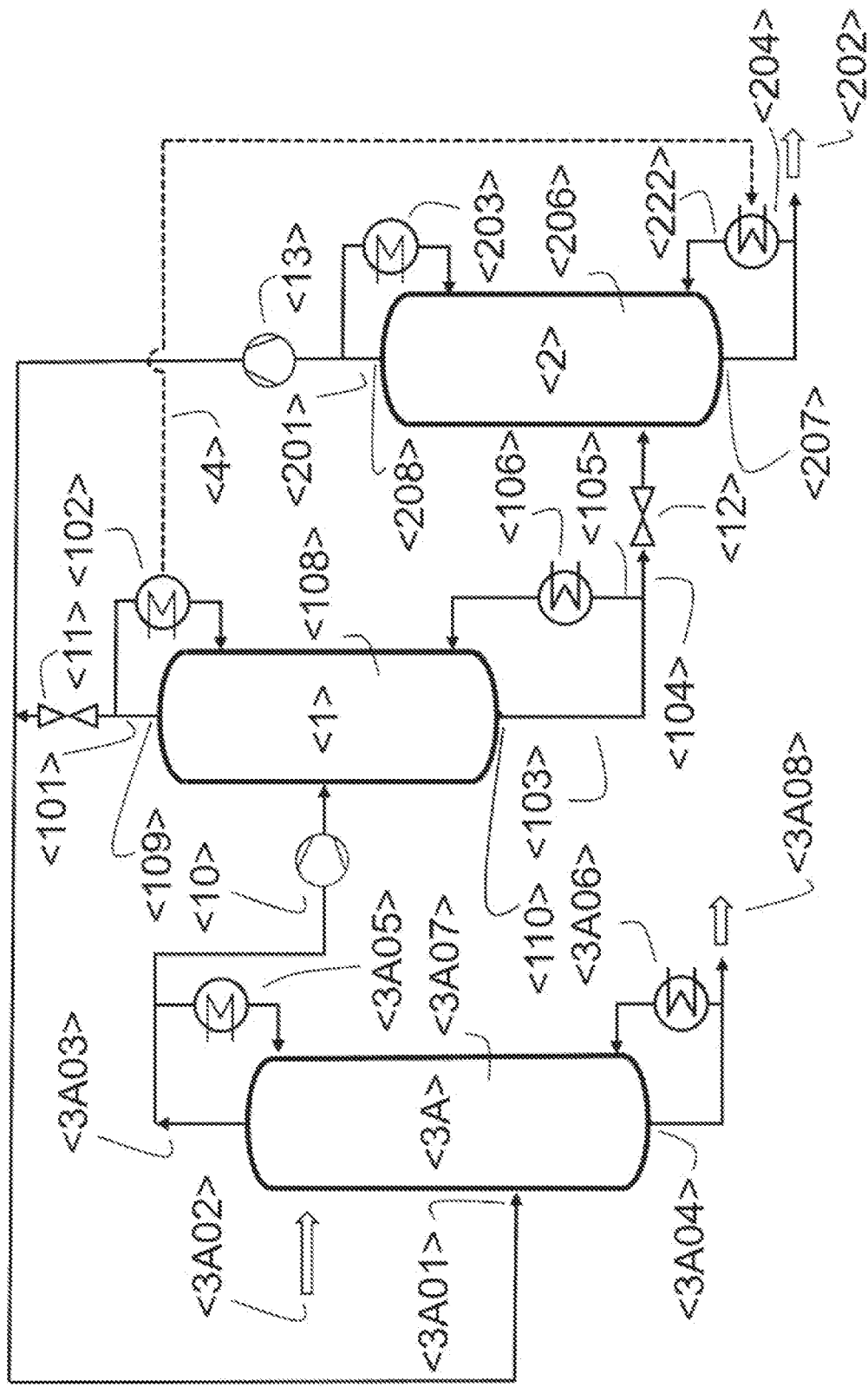
FIG. 1 shows a process according to the invention for producing alkali metal alkoxides with a corresponding interconnection of the rectification columns.

DETAILED DESCRIPTION OF THE INVENTION 4.1 Step (a1) of the Process According to the Invention In step (a1) of the process according to the invention for producing at least one alkali metal alkoxide of formula $M_AOR$ a reactant stream $S_{AE1}$ comprising ROH is reacted with a reactant stream $S_{AE2}$ comprising $M_AOH$ in countercurrent at a pressure $p_{3A}$ and a temperature $T_{3A}$ in a reactive rectification column $RR_A$ to afford a crude product $RP_A$ comprising $M_AOR$, water, ROH, $M_AOH$.

According to the invention, a "reactive rectification column" is a rectification column in which the reaction according to step (a1) or step (a2) of the process of the invention proceeds at least in some parts. It may also be abbreviated to "reaction column".

In step (a1) of the process according to the invention a bottoms product stream $S_{AP}$ comprising ROH and $M_AOR$ is withdrawn at the lower end of $RR_A$. A vapour stream SAO comprising water and ROH is withdrawn at the upper end of $RR_A$.

"Vapour stream" means that the respective stream is a gaseous stream.

In the process according to the invention, R is a $C_1$-$C_6$ hydrocarbon radical, preferably selected from the group consisting of methyl, ethyl, n-propyl, iso-propyl, n-butyl, sec-butyl, iso-butyl, tert-butyl, isomers of pentyl such as n-pentyl, more preferably selected from the group consisting of methyl, ethyl, n-propyl, iso-propyl, yet more preferably selected from the group consisting of methyl, ethyl. R is particularly preferably methyl and ROH is accordingly methanol.

$M_A$ is selected from sodium, potassium, preferably sodium.

The reactant stream $S_{AE1}$ comprises ROH. In a preferred embodiment the mass fraction of ROH in $S_{AE1}$ based on the total mass of the reactant stream $S_{AE1}$ is ≥95% by weight, yet more preferably ≥99% by weight, wherein Sm otherwise comprises especially water.

The alcohol ROH used as reactant stream $S_{AE1}$ in step (a1) of the process of the invention can also be a commercially available alcohol having a mass fraction of alcohol, based on the total mass of the reactant stream $S_{AE1}$, of more than 99.8% by weight and a mass fraction of water, based on the total mass of the reactant stream $S_{AE1}$, of up to 0.2% by weight.

The reactant stream $S_{AE1}$ is preferably introduced in vapour form.

The reactant stream $S_{AE2}$ comprises $M_AOH$. In a preferred embodiment $S_{AE2}$ comprises not only $M_AOH$ but also at least one further compound selected from water, ROH. $S_{AE2}$ more preferably comprises water in addition to $M_AOH$, in which case $S_{AE2}$ is then an aqueous solution of $M_AOH$.

When the reactant stream $S_{AE2}$ comprises $M_AOH$ and water the mass fraction of $M_AOH$ based on the total weight of the reactant stream $S_{AE2}$ is especially in the range from 10% to 55% by weight, preferably from 15% to 54% by weight, more preferably from 30% to 53% by weight and particularly preferably from 45% to 52% by weight, most preferably 50% by weight.

When the reactant stream $S_{AE2}$ comprises $M_AOH$ and ROH the mass fraction of $M_AOH$ based on the total weight of the reactant stream $S_{AE2}$ is especially in the range from 10% to 55% by weight, preferably from 15% to 54% by weight, more preferably from 30% to 53% by weight and particularly preferably from 45% to 52% by weight.

In the particular case in which the reactant stream $S_{AE2}$ comprises both water and ROH in addition to $M_AOH$ it is particularly preferable when the mass fraction of $M_AOH$ based on the total weight of the reactant stream $S_{AE2}$ is especially in the range from 10% to 55% by weight, preferably from 15% to 54% by weight, more preferably from 30% to 53% by weight and particularly preferably from 45% to 52% by weight.

Step (a1) of the process according to the invention is performed in a reactive rectification column (or "reaction column") $RR_A$.

Step (a2) of the process according to the Invention is performed in a reactive rectification column (or "reaction column") $RR_B$.

The reaction column $RR_A/RR_B$ preferably contains internals. Suitable internals are, for example, trays, structured packings or unstructured packings. When the reaction column $RR_A/RR_B$ contains trays, then bubble cap trays, valve trays, tunnel trays, Thormann trays, cross-slit bubble cap trays or sieve trays are suitable. When the reaction column $RR_A/RR_B$ contains trays it is preferable to choose trays where not more than 5% by weight, more preferably less than 1% by weight, of the liquid trickles through the respective trays. The constructional measures required to minimize trickle-through of the liquid are familiar to those skilled in the art. In the case of valve trays, particularly tightly closing valve designs are selected for example. Reducing the number of valves also makes it possible to increase the vapour velocity in the tray openings to twice the value typically established. When using sieve trays it is particularly advantageous to reduce the diameter of the tray openings while maintaining or even increasing the number of openings.

When using structured or unstructured packings, structured packings are preferred in terms of uniform distribution of the liquid. In this embodiment it is further preferable when in all parts of the column cross section corresponding to more than 2% of the total column cross section the average ratio of liquid stream to vapour stream is not exceeded by more than 15%, more preferably by more than 3%, in respect of the liquid. This minimized liquid amount makes it possible for the capillary effect at the wire meshes to eliminate local peaks of liquid trickling density.

For columns comprising unstructured packings, especially comprising random packings, and for columns comprising structured packings, the desired characteristics of the liquid distribution may be achieved when the liquid trickling density in the edge region of the column cross section adjacent to the column shell, corresponding to about 2% to 5% of the total column cross section, is reduced compared to the other cross-sectional regions by up to 100%, preferably by 5% to 15%. This can easily be achieved by, for example, targeted distributions of the drip points of the liquid distributors or the holes thereof.

The process according to the Invention may be carried out either continuously or discontinuously. It is preferably carried out continuously.

According to the invention "reaction of a reactant stream $S_{AE1}$ comprising ROH with a reactant stream $S_{AE2}$ comprising $M_AOH$ in countercurrent" is achieved, in particular, as a result of the feed point for at least a portion of the reactant stream $S_{AE1}$ comprising ROH in step (a1) being located on the reaction column $RR_A$ below the feed point of the reactant stream $S_{AE2}$ comprising $M_AOH$.

The reaction column $RR_A$ preferably comprises at least 2, in particular 15 to 40, theoretical plates between the feed point of the reactant stream $S_{AE1}$ and the feed point of the reactant stream $S_{AE2}$.

The reaction column $RR_A$ is preferably operated as a pure stripping column. Accordingly the reactant stream $S_{AE1}$ comprising ROH is especially supplied in vaporous form in the lower region of the reaction column $RR_A$. Step (a1) of the process according to the invention also comprises the case where a portion of the reactant stream $S_{AE1}$ comprising ROH is added in vapour form below the feed point of the reactant stream $S_{AE2}$ comprising $M_AOH$ but nevertheless at the upper end or in the region of the upper end of the reaction column $RR_A$. This makes it possible to reduce the dimensions of the lower region of the reaction column $RR_A$. When a portion of the reactant stream $S_{AE1}$ comprising ROH, in particular methanol, is added especially in vaporous form at the upper end or in the region of the upper end of the reaction column $RR_A$ only a fraction of 10% to 70% by weight, preferably of 30% to 50% by weight, (in each case based on the total amount of the alcohol ROH employed in step (a1) as $S_{AE1}$) is employed at the lower end of the reaction column $RR_A$ and the remaining fraction is added in vaporous form in a single stream or divided into a plurality of substreams preferably 1 to 10 theoretical trays, particularly preferably 1 to 3 theoretical trays, below the feed point of the reactant stream $S_{AE2}$ comprising $M_AOH$.

In the reaction column $RR_A$, the reactant stream $S_{AE1}$ comprising ROH is then reacted with the reactant stream $S_{AE2}$ comprising $M_AOH$ according to the reaction <1> described hereinabove to afford $M_AOR$ and $H_2O$, where these products are present in admixture with the reactants ROH and $M_AOH$ since an equilibrium reaction is concerned. Accordingly a crude product $RP_A$ which contains not only the products $M_AOR$ and water but also ROH and $M_AOH$ is obtained in the reaction column $RR_A$ in step (a1) of the process according to the invention.

The bottom product stream $S_{AP}$ comprising ROH and $M_AOR$ is obtained and withdrawn at the lower end of $RR_A$.

A water-containing alcohol stream, previously described as "vapour stream $S_{AB}$ comprising water and ROH", is withdrawn at the upper end of $RR_A$, preferably at the column top of $RR_A$.

The amount of the alcohol ROH comprised by the reactant stream $S_{AE1}$ is preferably chosen such that said alcohol also serves as a solvent for the alkali metal alkoxide $M_AOR$ obtained in the bottoms product stream $S_{AP}$. The amount of the alcohol ROH in the reactant stream $S_{AE1}$ is preferably chosen to achieve in the bottom of reaction column $RR_A$ the desired concentration of the alkali metal alkoxide solution which is withdrawn as a bottoms product stream $S_{AP}$ comprising ROH and $M_AOR$.

In a preferred embodiment of the process of the invention, especially in cases in which $S_{AE2}$ comprises water in addition to $M_AOH$, the ratio of the total weight (masses; unit: kg) of alcohol ROH used as reactant stream $S_{AE1}$ in step (a1) to the total weight (masses; unit: kg) of $M_AOH$ used as reactant stream $S_{AE2}$ in step (a1) is from 1:1 to 50:1, more preferably 5:1 to 48:1, yet more preferably 9:1 to 35:1, yet still more preferably 10:1 to 30:1, yet still more preferably 13:1 to 22:1, most preferably 14:1.

The reaction column $RR_A$ is operated with or without, preferably without, reflux.

"Without reflux" is to be understood as meaning that the vapour stream $S_{AB}$ withdrawn at the upper end of $RR_A$ comprising water and ROH is completely supplied to the first rectification column $RD_1$ according to step (b). The vapour stream $S_{AB}$ comprising water and ROH is preferably supplied to the first rectification column $RD_1$ in vaporous form.

"With reflux" is to be understood as meaning that the vapour stream $S_{AB}$ withdrawn at the upper end of the respective column, reaction column $RR_A$ in step (a1), comprising water and ROH is not completely discharged, i.e. is not completely supplied to the first rectification column $RD_1$ in step (b), but rather is at least partially, preferably partially, recycled to the respective column, reaction column $RR_A$ in step (a1), as reflux. In the cases where such a reflux is established, the reflux ratio is preferably 0.05 to 0.99, more preferably 0.1 to 0.9, yet more preferably 0.11 to 0.34, particularly preferably 0.14 to 0.27 and very particularly preferably 0.17 to 0.24. A reflux may be established by attaching to the top of the respective column, reaction column $RR_A$ in step (a1), a condenser $K_{RRA}$ in which the vapour stream $S_{AB}$ is at least partially condensed and sent back to the respective column, reaction column $RR_A$ in step a1). Generally and in the context of the present invention a reflux ratio is to be understood as meaning the ratio of the mass flow (kg/h) recycled to the respective column in liquid form (reflux) to the mass flow (kg/h) discharged from the respective column in liquid form (distillate) or gaseous form (vapours).

In the embodiment in which a reflux is established on the reaction column $RR_A$ the alcohol $M_AOH$ employed in step (a1) as reactant stream $S_{AE2}$ may also be at least partially, preferably partially, mixed with the reflux stream and the resulting mixture thus supplied to step (a1).

Step (a1) of the process according to the invention is in particular performed at a temperature $T_{3A}$ in the range from 25° C. to 200° C., preferably in the range from 45° C. to 150° C., more preferably in the range from 47° C. to 120° C. more preferably in the range from 60° C. to 110° C.

Step (a1) of the process according to the invention is in particular performed at a pressure $p_{3A}$ of 0.5 bar to 40 bar, preferably in the range from 0.75 bar to 5 bar, more preferably in the range from 1 bar to 2 bar, more preferably in the range from 1 bar to 1.8 bar, yet more preferably at 1.1 bar to 1.6 bar. It is an essential feature of the invention that when establishing the pressure $p_{3A}$: $p_1 > p_{3A}$. It is especially also the case that $p_{3A} > p_2$.

In a preferred embodiment the reaction column $RR_A$ comprises at least one evaporator which is in particular selected from intermediate evaporators $VZ_{3A}$ and bottoms evaporators $VS_{3A}$. The reaction column $RR_A$ particularly preferably comprises at least one bottoms evaporator $VS_{3A}$. Evaporators are special embodiments of heat exchangers WT.

Condensers K are likewise special embodiment of heat exchangers WT. Typical condensers are known to those skilled in the art. These are preferably employed as liquefiers at the top of rectification columns and reaction columns. In the direct energy transfer from the top stream of one column to the bottoms or intermediate stream of another column a condenser of one column may simultaneously be employed as an evaporator of the other column (as shown in the examples).

According to the invention "intermediate evaporators" VZ (for example $VZ_{3A}$ in $RR_A$, $VZ_{3B}$ in $RR_B$, $VZ_{RD1}$ in $RD_1$, $VZ_{RD2}$ in $RD_2$) are to be understood as meaning evaporators arranged above the bottom of the respective column, in particular above the bottom of the reaction column $RR_A$/$RR_B$ or above the bottom of the rectification column $RD_1$ or $RD_2$. They in particular evaporate crude product $RP_A$/$RP_B$ or $S_{RDX1Z}$ as sidestream.

According to the invention "bottoms evaporators" VS (for example $VS_{3A}$ at $RR_A$, $VS_{3B}$ at $RR_B$, $VS_{RD1}$ at $RD_1$, $VS_{RD2}$ at $RD_2$) are to be understood as meaning evaporators which heat the bottom of the respective column. In particular the bottom of the reaction column $RR_A$/$RR_B$ or rectification column $RD_1$ or $RD_2$. They evaporate bottoms product stream (for example $S_{AP}$/$S_{BP}$ or $S_{RDX1S}$).

A vaporizer is typically arranged outside the respective reaction column or rectification column. The mixture to be vaporized in the vaporizer is taken off from the column via an offtake or "offtake point" and fed to the at least one vaporizer.

The evaporated mixture is recycled back into the respective column, optionally with a residual proportion of liquid, via a feed or "feed point". When the evaporator is an intermediate evaporator the takeoff by means of which the respective mixture is withdrawn and supplied to the evaporator is a sidestream takeoff and the feed by means of which the evaporated respective mixture is sent back to the column is a sidestream feed. When the evaporator is a bottoms evaporator. i.e. heats the column bottom, at least a portion of the bottom takeoff stream is evaporated and recycled into the respective column in the region of the bottom.

However, it is alternatively also possible for example on a suitable tray when using an intermediate evaporator or in the bottom of the respective column to provide tubes which are traversed by the relevant heating medium. In this case, the vaporization occurs on the tray or In the bottom region of the column. However, it is preferable to arrange the vaporizer outside the respective column.

Suitable evaporators employable as intermediate evaporators and bottoms evaporators include for example natural circulation evaporators, forced circulation evaporators, forced circulation evaporators with decompression, steam boilers, falling film evaporators or thin film evaporators.

Heat exchangers for the vaporizer typically employed in the case of natural circulation evaporators and forced circulation evaporators are shell and tube or plate apparatuses. When using a shell and tube exchanger the heating medium may either flow through the tubes with the mixture to be evaporated flowing around the tubes or else the heating medium may flow around the tubes with the mixture to be evaporated flowing through the tubes. In the case of a falling-film evaporator, the mixture to be vaporized is typically introduced as a thin film on the inside of a tube and the tube is heated externally. In contrast to a falling-film evaporator, a thin-film evaporator additionally comprises a rotor with wipers which distributes the liquid to be evaporated on the inner wall of the tube to form a thin film.

In addition to the recited evaporator types it is also possible to employ any desired further evaporator type known to those skilled in the art and suitable for use on a rectification column.

When the reaction column $RR_A$/reaction column $RR_B$ comprises an intermediate evaporator $VZ_{3A}$ or $VZ_{3B}$ as it is preferable when the respective intermediate evaporator is arranged in the stripping region of the reaction column $RR_A$ in the region of the feed point of the reactant stream $S_{AE1}$ or in the case of the reaction column $RR_B$ in the region of the feed point for the reactant stream $S_{BE1}$. This makes it possible to introduce a predominant portion of the heat energy via the intermediate evaporator $VZ_{3A}$/$VZ_{3B}$. It is thus possible for example to introduce more than 80% of the energy via the intermediate vaporizer. According to the Invention the intermediate evaporator $VZ_{3A}$/$VZ_{3B}$ is preferably arranged and/or configured such that it introduces more than 50%, in particular more than 75%, of the total energy required for the reactive rectification.

When the reaction column $RR_A$/reaction column $RR_B$ has an intermediate evaporator $VZ_{3A}$ or $VZ_{3B}$ it is additionally advantageous when the intermediate evaporator is arranged such that the reaction column $RR_A$/$RR_B$ has 1 to 50 theoretical trays below the intermediate evaporator and 1 to 200 theoretical trays above the intermediate evaporator. It is especially preferred when the reaction column $RR_A$/$RR_B$ then has 2 to 10 theoretical trays below the intermediate evaporator and 20 to 50 theoretical trays above the intermediate evaporator.

When the reaction column $RR_A$/reaction column $RR_B$ comprises an intermediate evaporator $VZ_{3A}$/$VZ_{3B}$ it is also advantageous when the sidestream takeoff (i.e. the "takeoff point $E_{RRA}$" on the reaction column $RR_A$/the "takeoff point $E_{RRB}$" on the reaction column $RR_B$) by means of which the crude product $RP_A$/$RP_B$ is supplied to the intermediate evaporator $VZ_{3A}$/$VZ_{3B}$ and the sidestream feed (i.e. the "feed point $Z_{RRA}$" on the reaction column $RR_A$/the "feed point $Z_{RRB}$" on the reaction column $RR_B$) by means of which the evaporated crude product $RP_A$/$RP_B$ from the intermediate evaporator $VZ_{3A}$/$VZ_{3B}$ is sent back to the respective reaction column $RR_A$/$RR_B$ are positioned between the same trays of the reaction column $RR_A$/reaction column $RR_B$.

However, it is also possible for the sidestream takeoff and sidestream feed to be arranged at different heights.

In a preferred embodiment when using an Intermediate evaporator $VZ_{3A}/VZ_{3B}$ in $RR_A/RR_B$ the diameter of the reaction column $RR_A/RR_B$ above the intermediate evaporator $RR_A/RR_B$ is greater than the diameter of the reaction column $RR_A/RR_B$ below the intermediate evaporator $VZ_{3A}/VZ_{3B}$. This has the advantage of allowing capital expenditure savings.

In such an intermediate evaporator $VZ_{3A}/VZ_{3B}$ liquid crude product $RP_A$ comprising $M_AOR$, water, ROH, $M_AOH$ present in the reaction column $RR_A$ or liquid crude product $RP_B$ comprising $M_BOR$, water, ROH, $M_BOH$ present in the reaction column $RR_B$ may be converted into the gaseous state if already in the gaseous state heated further, thus improving the efficiency of the reaction of step (a1)/(a2) in the process according to the invention.

Arranging one or more intermediate evaporators $VZ_{3A}$ in the upper region of the reaction column $RR_A$ or one or more intermediate evaporators $VZ_{3B}$ in the upper region of the reaction column $RR_B$ makes it possible to reduce the dimensions in the lower region of the reaction column $RR_A/RR_B$. In the embodiment having at least one, preferably two or more, intermediate evaporators $VZ_{3A}/VZ_{3B}$ it is also possible to supply substreams of the ROH in liquid form in the upper region of the reaction column $RR_A/RR_B$.

According to the invention bottoms evaporators are arranged at the bottom of the reaction column $RR_A/RR_B$ and are then referred to as "$VS_{3A}$" and "$VS_{3B}$". Bottoms product stream $S_{AP}/S_{BP}$ present in the reaction column $RR_A/RR_B$ may be passed into such a bottoms evaporator and ROH at least partially removed therefrom to obtain a bottoms product stream $S_{AP*}$ having an elevated mass fraction of $M_AOR$ compared to $S_{AP}$/to obtain a bottoms product stream $S_{BP*}$ having an elevated mass fraction of $M_BOR$ compared to $S_{BP}$.

In step (a1) of the process according to the invention a bottoms product stream $S_{AP}$ comprising ROH and $M_AOR$ is withdrawn at the lower end of the reaction column $RR_A$.

It is preferable when the reaction column $RR_A$ comprises at least one bottoms evaporator $VS_{3A}$ through which the bottoms product stream $S_{AP}$ is then at least partially passed to at least partially remove ROH, thus affording a bottoms product stream $S_{AP*}$ having an elevated mass fraction of $M_AOR$ compared to $S_{AP}$.

The mass fraction of $M_AOR$ in the bottoms product stream $S_{AP*}$ is especially elevated compared to the mass fraction of $M_AOR$ in the bottoms product stream $S_{AP}$ by at least 1%, preferably by ≥2%, more preferably by ≥5%, yet more preferably by ≥10%, yet still more preferably by ≥20%, yet still more preferably by ≥30%, yet still more preferably by ≥40%, yet still more preferably by ≥50%, yet still more preferably by ≥100%, yet still more preferably by ≥150%.

It is preferable when $S_{AP}$ or, if at least one bottoms evaporator $VS_{3A}$ is used, through which the bottoms product stream $S_{AP}$ is at least partially passed to at least partially remove ROH, $S_{AP*}$ has a mass fraction of $M_AOR$ in ROH in the range from 1% to 50% by weight, preferably 5% to 32% by weight, more preferably 15% to 32% by weight, most preferably 30% to 32% by weight, in each case based on the total mass of $S_{AP}/S_{AP*}$.

The mass fraction of residual water in $S_{AP}/S_{AP*}$ is preferably <1% by weight, preferably <0.1% by weight, more preferably <0.01% by weight, based on the total mass of $S_{AP}/S_{AP*}$.

The mass fraction of reactant $M_AOH$ in $S_{AP}/S_{AP*}$ is preferably <1% by weight, preferably <0.1% by weight, more preferably <0.01% by weight, based on the total mass or $S_{AP}/S_{AP*}$.

4.2 Step (a2) of the Process According to the Invention (Optional)

According to the invention step (a2) is performed or not performed. In the optional step (a2), which proceeds simultaneously with and spatially separately from step (a1) of the process according to the Invention, a reactant stream $S_{BE1}$ comprising ROH is reacted with a reactant stream $S_{BE2}$ comprising $M_BOH$ in countercurrent at a pressure pau and a temperature $T_{3B}$ in a reactive rectification column $RR_B$ to afford a crude product mixture $RP_B$ comprising $M_BOR$, water, ROH, $M_BOH$.

In the optional step (a2) of the process according to the Invention a bottoms product stream $S_{BP}$ comprising ROH and $M_BOR$ is withdrawn at the lower end of $RR_B$. A vapour stream $S_{BB}$ comprising water and ROH is withdrawn at the top end of $RR_B$.

$M_B$ is selected from sodium, potassium, and preferably potassium.

The reactant stream $S_{BE1}$ comprises ROH. In a preferred embodiment the mass fraction of ROH in $S_{BE1}$ based on the total mass of the reactant stream $S_{BE1}$ is a ≥95% by weight, yet more preferably ≥99% by weight, wherein $S_{BE1}$ otherwise comprises especially water.

The alcohol ROH used as reactant stream $S_{BE1}$ in the optional step (a2) of the process of the Invention can also be a commercial alcohol having a mass fraction of alcohol, based on the total mass of the reactant stream $S_{BE1}$, of more than 99.8% by weight and a proportion by mass of water, based on the total mass of the reactant stream $S_{BE1}$, of up to 0.2% by weight.

The reactant stream $S_{BE1}$ is preferably introduced in vapour form.

The reactant stream $S_{BE2}$ comprises $M_BOH$. In a preferred embodiment $S_{BE2}$ comprises not only $M_BOH$ but also at least one further compound selected from water, ROH. It is yet more preferable when $S_{BE2}$ comprises water in addition to $M_BOH$, thus rendering $S_{BE2}$ an aqueous solution of $M_BOH$.

When the reactant stream $S_{BE2}$ comprises $M_BOH$ and water the mass fraction of $M_BOH$ based on the total weight of the reactant stream $S_{BE2}$ is especially in the range from 10% to 55% by weight, preferably from 15% to 54% by weight, more preferably from 30% to 53% by weight and particularly preferably from 45% to 52% by weight, most preferably 50% by weight.

When the reactant stream $S_{BE2}$ comprises $M_BOH$ and ROH the mass fraction of $M_BOH$ based on the total weight of the reactant stream $S_{BE2}$ is especially in the range from 10% to 55% by weight, preferably from 15% to 54% by weight, more preferably from 30% to 53% by weight and particularly preferably from 45% to 52% by weight.

In the particular case in which the reactant stream $S_{BE2}$ comprises both water and ROH in addition to $M_BOH$ it is particularly preferable when the mass fraction of $M_BOH$ based on the total weight of the reactant stream $S_{BE2}$ is especially in the range from 10% to 55% by weight, preferably from 15% to 54% by weight, more preferably from 30% to 53% by weight and particularly preferably from 45% to 52% by weight.

Step (a2) of the process according to the invention is performed in a reactive rectification column (or "reaction column") $RR_B$. Preferred embodiments of the reaction column $RR_B$ are described in section 4.1.

According to the invention "reaction of a reactant stream $S_{BE1}$ comprising ROH with a reactant stream $S_{BE2}$ comprising $M_BOH$ in countercurrent" is especially achieved as a result of the feed point for at least a portion of the reactant stream $S_{BE1}$ comprising ROH in optional step (a2) being arranged below the feed point for the reactant stream $S_{BE2}$ comprising $M_BOH$ on the reaction column $RR_B$.

The reaction column $RR_B$ preferably comprises at least 2, in particular 15 to 40, theoretical trays between the feed point of the reactant stream $S_{BE1}$ and the feed point of the reactant stream $S_{BE2}$.

The reaction column $RR_B$ is preferably operated as a pure stripping column. Accordingly the reactant stream $S_{BE1}$ comprising ROH is especially supplied in vaporous form in the lower region of the reaction column $RR_B$. The optional step (a2) of the process of the Invention also encompasses the case of part of the reactant stream $S_{BE1}$ comprising ROH being introduced in vapour form below the feed point of the reactant stream $S_{BE2}$ comprising alkaline solution $M_BOH$ but at the upper end or in the region of the upper end of the reaction column $RR_B$. This makes it possible to reduce the dimensions of the lower region of the reaction column $RR_B$. When a portion of the reactant stream $S_{BE1}$ comprising ROH, in particular methanol, is added especially in vaporous form at the upper end or in the region of the upper end of the reaction column $RR_B$ only a fraction of in particular 10% to 70% by weight, preferably of 30% to 50% by weight, (in each case based on the total amount of the alcohol ROH employed in optional step (a2)) is employed at the lower end of the reaction column $RR_B$ and the remaining fraction is added in vaporous form in a single stream or divided into a plurality of substreams preferably 1 to 10 theoretical trays, particularly preferably 1 to 3 theoretical trays, below the feed point of the reactant stream $S_{BE2}$ comprising $M_BOH$.

In the reaction column $RR_B$ the reactant stream $S_{BE1}$ comprising ROH is then reacted with the reactant stream $S_{BE1}$ comprising $M_BOH$ according to the reaction <1> described hereinabove to afford $M_BOR$ and $H_2O$, where these products are present in admixture with the reactants ROH and $M_BOH$ since an equilibrium reaction is concerned. Accordingly a crude product $RP_B$ which contains not only the products $M_BOR$ and water but also ROH and $M_BOH$ s obtained in the reaction column $RR_B$ in optional step (a2) of the process according to the invention.

The bottom product stream $S_{BP}$ comprising ROH and $M_BOR$ is obtained and withdrawn at the lower end of $RR_B$.

A water-containing alcohol stream, previously described as "vapor stream $S_{BB}$ comprising water and ROH", is withdrawn at the upper end of $RR_B$, preferably at the top or $RR_B$.

This vapour stream $S_{BB}$ comprising water and ROH is supplied to step (b) of the process according to the invention. Said stream is mixed with $S_{AB}$ before being supplied to step (b) of the process according to the invention or is not, i.e. is supplied to step (b) of the process according to the invention separately from $S_{AB}$. Vapour stream $S_{BB}$ is preferably mixed with $S_{AB}$ and the resulting mixed vapour stream is then introduced into step (b) of the process of the invention.

The amount of alcohol ROH present in the reactant stream $S_{BE1}$ is preferably selected so that it simultaneously serves as solvent for the alkali metal alkoxide $M_BOR$ present in the bottom product stream $S_{BP}$. The amount or the alcohol ROH in the reactant stream $S_{BE1}$ is preferably chosen to achieve in the bottom of the reaction column the desired concentration of the alkali metal alkoxide solution which is withdrawn as a bottoms product stream $S_{BP}$ comprising ROH and $M_BOR$.

In a preferred embodiment of optional step (a2) of the process according to the Invention, and especially in the cases where $S_{BE2}$ comprises water in addition to $M_BOH$, the ratio of the total weight (masses; units: kg) of alcohol employed in step (a2) as reactant stream $S_{BE1}$ ROH to the total weight (masses; unit: kg) of $M_BOH$ employed in step (a2) as reactant stream $S_{BE2}$ is 1:1 to 50:1, more preferably 5:1 to 48:1, yet more preferably 9:1 to 35:1, yet still more preferably 10:1 to 30:1, yet still more preferably 13:1 to 22:1, most preferably 14:1.

The reaction column $RR_B$ is operated with or without, preferably without, reflux.

"Without reflux" is to be understood as meaning that the vapour stream $S_{BB}$ withdrawn at the upper end of $RR_B$ comprising water and ROH is completely supplied to the rectification column $RD_1$ according to step (b). The vapour stream $S_{BB}$ comprising water and ROH is preferably supplied to the rectification column $RD_1$ in vaporous form.

"With reflux" is to be understood as meaning that the vapor stream $S_{BB}$ withdrawn at the upper end of the respective column, reaction column $RR_B$ in step (a2), comprising water and ROH is not completely discharged, i.e. is not completely supplied to the first rectification column $RD_1$ in step (b), but rather is at least partially, preferably partially, recycled to the respective column, reaction column $RR_B$ in step (a2), as reflux. In the cases where such a reflux is established the reflux ratio is preferably 0.05 to 0.99, more preferably 0.1 to 0.9, yet more preferably 0.11 to 0.34, particularly preferably 0.14 to 0.27 and very particularly preferably 0.17 to 024. A reflux may be established by attaching at the top of the respective column, reaction column $RR_B$ in step (a2), a condenser $K_{RRB}$ in which the vapour stream $S_{BB}$ is at least partially condensed and sent back to the respective column, reaction column $RR_B$ in step (a2).

In the embodiment in which a reflux is established on the reaction column $RR_B$ the alcohol $M_BOH$ employed in optional step (a2) as reactant stream $S_{BE2}$ may also be at least partially, preferably partially, mixed with the reflux stream and the resulting mixture thus supplied to step (a2).

Optional step (a2) of the process according to the invention is in particular performed at a temperature $T_{3B}$ in the range from 25° C. to 200° C., preferably in the range from 45° C. to 150° C., more preferably in the range from 47° C. to 120° C., more preferably in the range from 60° C. to 110° C.

Optional step (a2) of the process according to the invention is in particular performed at a pressure $p_{3B}$ of 0.5 bar to 40 bar, preferably in the range from 0.75 bar to 5 bar, more preferably in the range from 1 bar to 2 bar, more preferably in the range from 1 bar to 1.8 bar, yet more preferably at 1.1 bar to 1.8 bar. It is an essential feature of the invention that when establishing the pressure $p_{3B}$: $p_1 > p_{3B}$. It is especially also the case that $p_{3B} > p_2$.

In a preferred embodiment the reaction column $RR_B$ comprises at least one evaporator which is in particular selected from intermediate evaporators $V_{AB}$ and bottoms evaporators $V_{SB}$. The reaction column $RR_B$ particularly preferably comprises at least one bottoms evaporator $VS_{3B}$.

In optional step (a2) of the process according to the invention a bottoms product stream $S_{BP}$ comprising ROH and $M_BOR$ is withdrawn at the lower end of the reaction column $RR_B$.

It is preferable when the reaction column $RR_B$ comprises at least one bottoms evaporator $VS_{3B}$ through which the bottoms product stream $S_{BP}$ is then at least partially passed to at least partially remove ROH, thus affording a bottoms product stream $S_{BP*}$ having an elevated mass fraction of $M_BOR$ compared to $S_{BP}$.

The mass fraction of $M_B$ OR in the bottoms product stream $S_{BP*}$ is especially elevated compared to the mass fraction of $M_B$ OR in the bottoms product stream $S_{BP}$ by at least 1%, preferably by ≥2%, more preferably by ≥5%, yet more preferably by ≥10%, yet still more preferably by ≥20%, yet still more preferably by ≥30%, yet still more preferably by ≥40%, yet still more preferably by a ≥50%, yet still more preferably by ≥100%, yet still more preferably by ≥150%.

It is preferable when $S_{BP}$ or, if at least one bottoms evaporator $VS_{3B}$ is used, through which the bottoms product stream $S_{BP}$ is at least partially passed to at least partially remove ROH, $S_{BP*}$ has a mass fraction of $M_B$ OR in ROH in the range from 1% to 50% by weight, preferably 5% to 32% by weight, more preferably 10% to 32% by weight, most preferably 15% to 30% by weight, in each case based on the total mass of $S_{BP}/S_{BP*}$.

The mass fraction of residual water in $S_{BP}/S_{BP*}$ is preferably <1% by weight, preferably <0.1% by weight, more preferably <0.01% by weight, based on the total mass of $S_{BP}/S_{BP*}$.

The mass fraction of reactant $M_BOH$ in $S_{BP}/S_{BP*}$ is preferably <1% by weight, preferably <0.1% by weight, more preferably <0.01% by weight, based on the total mass of $S_{BP}/S_{BP*}$.

In the embodiments of the present process in which step (a2) is also performed it is preferable when the bottoms product stream $S_{AP}$ is at least partially passed through a bottoms evaporator $VS_{3A}$ and ROH is at least partially removed from SA to afford a bottoms product stream $S_{AP*}$ having an elevated mass fraction of $M_AOR$ compared to $S_{AP}$ and/or, preferably and, the bottoms product stream $S_{BP}$ is at least partially passed through a bottoms evaporator $VS_{3B}$ and ROH is at least partially removed from $S_{BP}$ to afford a bottoms product stream $S_{BP*}$ having an elevated mass fraction of $M_BOR$ compared to $S_{BP}$.

In the embodiments of the present invention in which it is performed step (a2) of the process according to the invention is performed simultaneously with and spatially separate from step (a1). Spatial separation is ensured by performing steps (a1) and (a2) in the two reaction columns $RR_A$ and $RR_B$.

In an advantageous embodiment of the invention the reaction columns $RR_A$ and $RR_B$ are accommodated in one column shell, where the column is at least partially subdivided by at least one dividing wall. Such a column having at least one dividing wall will according to the invention be referred to as "DWC". Such dividing wall columns are familiar to those skilled in the art and are described for example in U.S. Pat. No. 2,295,258, EP 0 122 387 A2, EP 0 128 288 A2, WO 2010/097318 A1 and I. Dejanović, Lj. Matijašević, Ž. Olujić, *Chemical Engineering and Processing* 2010, 49, 559-580. In the dividing wall columns suitable for the process according to the invention the dividing walls preferably extend to the floor and, in particular, preferably span at least a quarter, more preferably at least a third, yet more preferably at least half, yet more preferably at least two thirds, yet still more preferably at least three quarters, of the column by height They divide the columns into at least two reaction spaces in which spatially separate reactions may be carried out. The reaction spaces provided by the at least one dividing wall may be of identical or different sizes.

In this embodiment the bottoms product streams $S_{AP}$ and $S_{BP}$ may be separately withdrawn in the respective regions separated by the dividing wall and preferably passed through the bottoms evaporator $VS_{3A}/VS_{3B}$ attached for each reaction space formed by the at least one reaction wall in which ROH is at least partially removed from $S_{AP}/S_{BP}$ to afford $S_{AP*}/S_{BP*}$.

4.3 Step (b) of the Process According to the Invention

In step (b) of the process according to the invention the vapour stream $S_{AB}$ and if step (a2) is performed the vapour stream $S_{BB}$ in admixture with $S_{AB}$ or separately from $S_{AB}$ is passed into a first rectification column $RD_1$,
to obtain a mixture $G_{RD1}$ comprising water and ROH in the rectification column $RD_1$.

In the optional embodiment of the process according to the invention in which step (a2) is performed the vapour stream $S_{BB}$ is preferably mixed with $S_{AB}$ and the obtained mixed vapour $S_{ABB}$ then introduced into a rectification column $RD_1$.

In one embodiment of the present invention (when $p_{3A}<p_1/p_{3B}<p_1$) the vapour stream $S_{AB}$ and, in cases where the optional step (a2) is performed, the vapour stream $S_{BB}$ may be compressed before they are passed into the rectification column $RD_1$. This may be effected via a compressor $VD_{31}$. However, in the embodiments of the present invention in which $p_{3A}>p_1$ and $p_{3B}>p_1$ the provision of a compressor $VD_{31}$ is not necessary and it is therefore possible to save on the provision thereof and the electrical energy required therefor.

It will be appreciated that even in the embodiments in which the optional step (a2) is performed and $S_{BB}$ is introduced into the rectification column $RD_1$ separately from $S_{AB}$ $S_{AB}$ and $S_{BB}$ undergo mixing in the rectification column $RD_1$ with the result that a mixture $G_{RD1}$ comprising water and ROH is always obtained in the first rectification column $RD_1$ after performance of step (b).

Any desired rectification column known to those skilled in the art may be employed as rectification column $RD_1$ in step (b) of the process according to the invention. The rectification column $RD_1$ preferably contains internals. Suitable internals are, for example, trays, unstructured packings or structured packings. As trays, use is normally made of bubble cap trays, sieve trays, valve trays, tunnel trays or slit trays. Unstructured packings are generally beds of random packing elements. Packing elements normally used are Raschig rings, Pall rings, Berl saddles or Intalox® saddles. Structured packings are for example marketed under the trade name Mellapack® from Sulzer. Apart from the internals mentioned, further suitable internals are known to a person skilled in the art and can likewise be used.

Preferred internals have a low specific pressure drop per theoretical plate. Structured packings and random packing elements have, for example, a significantly lower pressure drop per theoretical plate than trays. This has the advantage that the pressure drop in the rectification column remains as low as possible and the mechanical power of the compressor and the temperature of the alcohol/water mixture $G_{RD1}$ to be evaporated thus remains low.

When the rectification column $RD_1$ contains structured packings or unstructured packings these may be divided or in the form of an uninterrupted packing. However, typically at least two packings are provided, one packing above the feed point of the vapour stream $S_{AB}$/the feed points of the two vapour streams $S_{AB}$ and $S_{BB}$ and a packing below the feed point of the vapour stream $S_{AB}$/the feed points of the two vapour streams $S_{AB}$ and $S_{BB}$/the feed point of the mixed vapours $S_{ABB}$. If an unstructured packing is used, for example a random packing, the random packing elements are typically disposed on a suitable sieve tray or mesh tray.

At the end or step (b) of the process according to the invention a mixture $G_{RD1}$ comprising water and ROH is finally obtained in the rectification column $RD_1$. The composition of the mixture $G_{RD1}$ results in particular from the composition of the vapour stream $S_{AB}$ in particular and if step (a2) is performed partly from the composition of the two vapour streams $S_{AB}$ and $S_{BB}$ in particular.

4.4 Step (c) of the Process According to the Invention

In step (c) of the process according to the invention the mixture $G_{RD1}$ comprising water and ROH is in the first rectification column $RD_1$ at a pressure $p_1$ and a temperature $T_1$ separated into an ROH-comprising vapour stream $S_{RDB1}$ at the upper end (=top) of $RD_1$ and a bottoms stream $S_{RDS1}$ comprising water and ROH at the lower end (=bottom) of $RD_1$.

With the exception of the proviso that $p_1 > p_2$ the pressure $p_1$ in $RD_1$ may be chosen by those skilled in the art according to their knowledge of the art. It is preferably in the range between 1 bar and 20 bar, preferably 1 bar and 15 bar, more preferably 2 to 14 bar, yet more preferably 4.00 to 11.00 bar, yet more preferably 6.00 to 10.00 bar, yet more preferably 7.00 to 8.90 bar, wherein, simultaneously, $p_1 > p_2$.

The temperature $T_1$ in $RD_1$ may be chosen by those skilled in the art according to their knowledge of the art. It is preferably in the range from 40° C. to 220° C., preferably from 60° C. to 190° C.

In a preferred embodiment $p_{3A} > p_2$ and in addition in cases where step (a2) is performed $p_{3B} > p_2$. As a result of this established pressure the total energy demand of the process is surprisingly minimized compared to the embodiments where $p_{3A} < p_2/p_{3B} < p_2$ The separation according to step (c) of the process according to the invention is a distillative separation of the alcohol/water mixture $G_{RD1}$ as is known to those skilled in the art.

At the lower end (also: "bottom") of the rectification column $RD_1$ a bottoms stream $S_{RDS1}$ still comprising alcohol ROH is obtained. $S_{RDS1}$ comprises ROH in a mass fraction of in particular 0.005% to 95% by weight, preferably 25% to 95% by weight, based on the total mass of $S_{RDS1}$. $S_{RDS1}$ preferably comprises essentially water in addition to the alcohol ROH.

In a preferred embodiment of the Invention $S_{RDB1}$ is at least partially employed as reactant stream $S_{AE1}$ in the reactive rectification column $RR_A$ and if step (a2) is performed alternatively or in addition employed as reactant stream $S_{BE1}$ in the reactive rectification column $RR_B$.

Also obtained at the top of the rectification column $RD_1$ is the vapour stream $S_{RDB1}$ comprising ROH. The preferred mass fraction of ROH in this vapour stream $S_{RDB1}$ is ≥99% by weight, preferably ≥99.6% by weight, more preferably ≥99.9% by weight, in each case based on the total mass of $S_{RDB1}$, wherein the remainder is especially water.

In step (c) the vapour $S_{AB}$ or $S_{AB}$ and $S_{BB}$ obtained in step (a1) or step (a1) and (a2) is subjected to distillative separation. These vapours comprise essentially the alcohol ROH and water. In particular, $S_{AB}$ or $S_{AB}$ and $S_{BB}$ are each a water/alcohol mixture in which the mass fraction of ROH is preferably in the range >80% by weight, more preferably >85% by weight, yet more preferably >90% by weight (based on the total mass of $S_{AB}$ or $S_{AB}$ and $S_{BB}$). Thus in particular $G_{RD1}$ too is an alcohol/water mixture in which the mass fraction of ROH is preferably in the range >80% by weight, more preferably >95% by weight, yet more preferably >90% by weight (based on the total mass of $G_{RD1}$).

4.5 Step (d) of the Process According to the Invention

In step (d) of the process according to the invention the bottoms stream $S_{RDS1}$ is completely or partially, preferably partially, passed into a second rectification column $RD_2$.

This affords a mixture $G_{RD2}$ comprising water and ROH in the second rectification column $RD_2$.

In the embodiment of the present invention in which $S_{RDS1}$ is partially passed into $RD_2$ this is especially performed such that a first portion $S_{RDS11}$ of the bottoms stream $S_{RDS1}$ discharged from the first rectification column $RD_1$ is passed into a second rectification column $RD_2$ and a second portion $S_{RDS12}$ of the bottoms stream $S_{RDS1}$ discharged from the first rectification column $RD_1$ is recycled into the first rectification column $RD_1$. It is yet more preferable when energy is transferred to $S_{RDS12}$, yet still more preferable when $S_{RDS12}$ is heated. Once $S_{RDS12}$ has been recycled to $RD_1$ it undergoes mixing in $RD_1$ with $G_{RD1}$ and thus provides energy for separating $G_{RD1}$ according to step (c).

In this preferred embodiment of step (d) of the process according to the invention it is yet more preferable when the ratio of the masses (in kg) of $S_{RDS11}$ to $S_{RDS12}$ are in the range 9:1 to 1:9, yet more preferably 4:1 to 1:4, yet more preferably 7:3 to 3:7, yet more preferably 3:2 to 2:3, yet more preferably 1:1.

In this preferred embodiment of step (d) of the process according to the invention it is possible to supply energy to the stream $S_{RDS12}$. In a preferred embodiment this is effected when the stream $S_{RDS12}$ is passed through a bottoms evaporator $VS_{RD1}$ in which energy is transferred from a heat transfer medium to $S_{RDS12}$. This energy transfer may advantageously be undertaken when $S_{RDS12}$ and the heat transfer medium are passed through a bottoms evaporator $VS_{RD1}$. After the recycling of $S_{RDS12}$ into the reaction column $RR_A$ $S_{RDS12}$ then transfers the energy to $G_{RD1}$.

Any desired rectification column known to those skilled in the art may be employed as rectification column $RD_2$ in step (d) of the process according to the invention. The rectification column $RD_2$ preferably contains internals. Suitable internals are, for example, trays, unstructured packings or structured packings. As trays, use is normally made of bubble cap trays, sieve trays, valve trays, tunnel trays or silt trays. Unstructured packings are generally beds of random packing elements. Packing elements normally used are Raschig rings, Pall rings, Berl saddles or Intalox® saddles. Structured packings are for example marketed under the trade name Mellapack® from Sulzer. Apart from the internals mentioned, further suitable internals are known to a person skilled in the art and can likewise be used.

Preferred internals have a low specific pressure drop per theoretical plate. Structured packings and random packing elements have, for example, a significantly lower pressure drop per theoretical plate than trays. This has the advantage that the pressure drop in the rectification column $RD_2$ remains as low as possible and the mechanical power of the compressor and the temperature of the alcohol/water mixture $G_{RD2}$ to be evaporated remains low.

When the rectification column $RD_2$ contains structured packings or unstructured packings these may be divided or in the form of an uninterrupted packing. However, typically at least two packings are provided, one packing above the feed point of the stream $S_{RDS1}$/the portion of $S_{RDS1}$, in particular $S_{RDS12}$, and one packing below the relevant feed point. If an unstructured packing is used, for example a random packing, the random packing elements are typically disposed on a suitable sieve tray or mesh tray.

$S_{RDS1}$/the portion of $S_{RDS1}$ which is passed into $RD_2$ and which is preferably $S_{RDS12}$ is at least partially liquid.

Passage thereof into $RD_2$ via a liquid compressor or a pump P is thus further preferred.

At the end of step (d) of the process according to the invention a mixture $G_{RD2}$ comprising water and ROH is finally obtained in the rectification column $RD_2$. The composition of the mixture $G_{RD2}$ results especially from the composition of the stream $S_{RDS1}$/the portion of the stream $S_{RDS1}$, preferably $S_{RDS12}$, which is passed into $RD_2$.

4.6 Step (e) of the Process According to the Invention

In step (e) of the process according to the invention the mixture $G_{RD2}$ comprising water and ROH is at a pressure $p_2$ and a temperature $T_2$ separated into an ROH-comprising vapour stream $S_{RDB2}$ at the top of $RD_2$ and a bottoms stream $S_{RDS2}$ comprising water and optionally ROH at the bottom of $RD_2$.

With the exception of the proviso that $p_1 > p_2$ the pressure $p_2$ in $RD_2$ may be chosen by those skilled in the art according to their knowledge of the art. It is preferably in the range between 1 bar and 20 bar, preferably 1 bar and 15 bar, more preferably 1 to 10 bar, yet more preferably 1.00 to 2.00 bar, yet more preferably 1.10 to 1.80 bar, yet more preferably 1.10 to 1.50 bar, wherein, simultaneously, $p_1 > p_2$.

The temperature $T_2$ in $RD_2$ may be chosen by those skilled in the art according to their knowledge of the art. It is preferably in the range from 40° C. to 220° C., preferably from 60° C. to 190° C.

The separation according to step (e) of the process according to the Invention is a distillative separation of the alcohol/water mixture $G_{RD2}$ as is known to a person skilled in the art.

Obtained at the bottom of the rectification column $RD_2$ is a stream $S_{RDS2}$ which may comprise <1% by weight of alcohol based on the total mass of $S_{RDS2}$.

Also obtained at the top of the rectification column $RD_2$ is the vapour stream $S_{RDB2}$ comprising ROH. The preferred mass fraction of ROH in this vapour stream $S_{RDB2}$ is ≥99% by weight, preferably ≥99.6% by weight, more preferably ≥99.9% by weight, in each case based on the total mass of $S_{RDB2}$, wherein the remainder is especially water.

In a preferred embodiment of the present invention $S_{RDB2}$ is at least partially employed as reactant stream $S_{AE1}$ in the reactive rectification column $RR_A$ and if step (a2) is performed alternatively or in addition employed as reactant stream $S_{BE1}$ in the reactive rectification column $RR_B$.

In step (e) the stream $S_{RDS2}$, preferably the portion $S_{RDS12}$, completely or partially passed into the second rectification column $RD_2$ in step (d) is subjected to distillative separation.

4.7 Pressure Management as a Characterizing Feature

The process according to the invention is characterized in that during operation of the rectification columns $RD_1$ (step (c)) and $RD_2$ (step (e)) a certain pressure ratio is established.

Accordingly, $p_1 > p_2$, $p_1 > p_{3A}$ and in the cases where step (a2) is performed $p_1 > p_{3B}$.

It has surprisingly been found that maintaining these pressures allows the demand for energy to be supplied in the form of heating steam to be minimized and the majority of the energy required for the process to be covered through electricity.

It is yet more advantageous when in addition the pressures are established such that $p_{3A} > p_2$ and in cases where step (a2) is performed in addition $p_{3B} > p_2$. Establishing the pressures $p_{3A}$ and $p_{3B}$ in such a way reduces the altogether required energy demand compared to the case where $p_{3A} < p_2 / p_{3B} < p_2$.

4.8 Characterizing Step (f): Enemy Transfer from $S_{RDB2}$ to $G_{RD1}$

The step (f) of the process according to the Invention which is characterizing in addition to the pressure regime is that energy is transferred from $S_{RDB1}$ to the mixture $G_{RD2}$ in the second rectification column $RD_2$. According to the Invention "energy transfer" is in particular to be understood as meaning "heat transfer".

This step (f) and the pressure regime according to the invention allow a particularly advantageous integration of the energy which would otherwise dissipate which makes it possible to cover a particularly large portion of the energy demand of the process through electricity instead of heating steam. This makes the process according to the invention particularly energy-efficient.

According to the invention the transfer of energy from $S_{RDB1}$ to $G_{RD2}$ in $RD_2$ may be effected in various ways familiar to those skilled in the art and preferably comprises heating $G_{RD2}$ in $RD_2$ with $S_{RDB1}$, for example via a heat transfer medium WT.

According to the invention in step (f) the energy is especially transferred from $S_{RDB2}$ to $G_{RD2}$ in $RD_2$ directly or indirectly, preferably directly.

4.8.1 Direct Energy Transfer from $S_{RDB1}$ to $G_{RD2}$ in $RD_2$

According to the invention "direct energy transfer from $S_{RDB1}$ to $G_{RD2}$ in $RD_2$" is to be understood as meaning that an energy transfer, preferably heating, of $G_{RD2}$ in $RD_2$ with $S_{RDB1}$ is effected such that $G_{RD2}$ is contacted with $S_{RDB1}$ without $G_{RD2}$ undergoing mixing with $S_{RDB1}$, thus transferring energy from $S_{RDB1}$ to $G_{RD2}$. However, direct energy transfer according to the invention is to be understood as also including cases where an energy transfer, preferably heating, of a stream $S_X$ discharged from $RD_2$ with $S_{RDB1}$ is effected without $S_{RDB1}$ undergoing mixing with $S_X$, thus transferring energy from $S_{RDB1}$ to $S_X$, and $S_X$ is then passed back into $RD_2$ where it undergoes mixing with $G_{RD2}$ in $RD_2$ and thus transfers the energy absorbed from $S_{RDB1}$ to $G_{RD2}$ in $RD_2$.

In a particular embodiment of the present invention $S_X$ is selected from the group consisting of $S_{RDS22}$, $S_{RDX2}$.

Contacting without mixing is achieved by processes known to those skilled in the art, for example by contacting via a dividing wall made of metal, plastic etc., in particular in a heat exchanger WT, preferably a condenser K or evaporator V which is in particular selected from bottoms evaporators VS and intermediate evaporators VZ.

According to the invention it is preferable when direct energy transfer from $S_{RDB1}$ to the mixture $G_{RD2}$ in the second rectification column $RD_2$ is performed according to at least one of the steps (α-i), (α-ii), (α-iii), more preferably according to at least one of the steps (α-i), (α-ii).

(α-i) energy from $S_{RDB1}$ is transferred to a portion $S_{RDS22}$ of the bottoms stream $S_{RDS2}$ discharged from $RD_2$ and $S_{RDS22}$ is then recycled into $RD_2$. This step (α-i) also comprises embodiments in which energy is initially transferred from $S_{RDB1}$, preferably via a heat exchanger WT, to the overall bottoms stream $S_{RDS2}$ and the portion $S_{RDS22}$ is only then separated from the bottoms stream $S_{RDS2}$ and subsequently $S_{RDS22}$ is recycled into $RD_2$.

(α-ii) at least one stream $S_{RDX2}$ distinct from $S_{RDB2}$ and $S_{RDS2}$ comprising ROH and water is discharged from $RD_2$, energy is then transferred from $S_{RDS1}$ to $S_{RDX2}$, preferably via a heat exchanger WT, and $S_{RDX2}$ is recycled into $RD_2$.

It is preferable when $S_{RDX2}$ is withdrawn below the vapour stream $S_{RDB2}$ on $RD_2$. $S_{RDX2}$ is then especially selected from bottoms stream $S_{RDX2S}$, intermediate stream $S_{RDX2Z}$.

A bottoms stream $S_{RDX2S}$ is a stream whose withdrawal point $RD_2$ is at the same height or below the withdrawal point of $S_{RDS2}$. $S_{RDX2S}$ may then be passed through a heat exchanger WT, in particular a bottoms evaporator VS, and energy transferred therein from $S_{RDS1}$ to $S_{RDX2S}$.

An intermediate stream $S_{RDX2Z}$ is a stream whose withdrawal point on $RD_2$ is between the withdrawal points of $S_{RDB2}$ and $S_{RDS2}$. $S_{RDX2Z}$ may then be discharged from $RD_2$ and passed through a heat exchanger WT, in particular an intermediate evaporator VZ, and energy transferred from $S_{RDB1}$ to $S_{RDX2Z}$ therein.

(α-iii) $S_{RDB1}$ is passed through $RD_2$, thus transferring energy from $S_{RDB1}$ to $G_{RD2}$, preferably via a heat exchanger WT. Such an embodiment may be realized for example when $S_{RDB1}$ is passed through the rectification column $RD_2$ through a conduit whose surface $S_{RDB1}$ transfers energy to $G_{RD2}$ in $RD_2$.

4.8.2 Indirect Energy Transfer from $S_{RDB1}$ to $G_{RD2}$ in $RD_2$

According to the invention "indirect energy transfer from $S_{RDB1}$ to $G_{RD2}$ in $RD_2$" is to be understood as meaning that an energy transfer, preferably heating, of $G_{RD2}$ with $S_{RDB1}$ is effected in $RD_2$ such that $G_{RD2}$ is not directly contacted with $S_{RDB1}$ but rather at least one additional, preferably precisely one additional, heat transfer medium $W_1$ distinct from $G_{RD2}$ and $S_{RDB1}$ is employed which during energy transfer from $S_{RDB1}$ to $G_{RD2}$ in $RD_2$ undergoes mixing neither with $S_{RDB1}$ nor with $G_{RD2}$ in $RD_2$. Energy is transferred from $S_{RDB1}$ to the at least one heat exchanger $W_1$ without $S_{RDB1}$ and the at least one heat exchanger $W_1$ undergoing mixing and then transferred from the at least one heat transfer medium $W_1$ to $G_{RD2}$ in $RD_2$ without the at least one heat exchanger $W_1$ and $G_{RD2}$ undergoing mixing.

Indirect energy transfer according to the invention is to be understood as also including cases where energy is transferred from $S_{RDB1}$ to the at least one, preferably precisely one, heat transfer medium $W_1$ without $S_{RDB1}$ and the at least one heat exchanger $W_1$ undergoing mixing and subsequently an energy transfer, preferably heating, of a stream $S_X$ discharged from $RD_2$ with the at least one heat transfer medium $W_1$ is effected without the at least one heat transfer medium $W_1$ undergoing mixing with $S_X$, thus transferring energy from the at least one heat transfer medium $W_1$ to $S_X$, and $S_X$ is then recycled into $RD_2$ where it undergoes mixing with $G_{RD2}$ in $RD_2$ and thus transfers the energy absorbed by $S_{RDB1}$ via the at least one heat transfer medium $W_1$ to $G_{RD2}$ in $RD_2$.

In a particular embodiment of the present invention $S_X$ is selected from the group consisting of $S_{RDS22}$, $S_{RDX2}$.

"At least one heat transfer medium $W_1$" comprises the cases where the energy of $W_1$ is first transferred to one or more further heat transfer media $W_2$, $W_3$, $W_4$, $W_5$ etc. distinct from $G_{RD2}$ and $S_{RDB1}$ and the last of these heat transfer media, referred to as "$W_Y$" is contacted with $G_{RD2}$ in $RD_1$, thus transferring energy, preferably heat, from $W_Y$ to $G_{RD2}$ but without $W_Y$ and $G_{RD2}$ undergoing mixing. Energy, preferably heat, may likewise be transferred from $W_Y$ to a stream $S_X$ discharged from $RD_2$ without $W_Y$ and $S_X$ undergoing mixing and $S_X$ subsequently recycled into $RD_2$ where it undergoes mixing with $G_{RD2}$ in $RD_2$, thus transferring the energy absorbed by $W_Y$ to $G_{RD2}$ in $RD_2$.

The described contacting is in each case preferably performed in a heat exchanger WT, preferably a condenser K or evaporator V, which is especially selected from bottoms evaporators VS and intermediate evaporators VZ.

According to the invention it is preferable when indirect energy transfer from $S_{RDB1}$ to the mixture $G_{RD2}$ in the second rectification column $RD_2$ is performed according to at least one of the steps (β-i), (β-ii), (β-iii), more preferably according to at least one of the steps (β-i), (β-ii).

(β-i) a portion $S_{RDS22}$ of the bottoms stream $S_{RDS2}$ discharged from $RD_2$ is recycled into the second rectification column $RD_2$. Energy is transferred from $S_{RDB1}$ to at least one heat transfer medium $W_{i1}$ distinct from $S_{RDS22}$ and then transferred from the at least one heat transfer medium $W_{i1}$ to $S_{RDS22}$ and $S_{RDS22}$ is then recycled into $RD_2$:

This step (β-i) also comprises embodiments in which energy is initially transferred from the at least one, preferably precisely one, heat transfer medium $W_{i1}$ distinct from $S_{RDS22}$, preferably via a heat exchanger WT, to the overall bottoms stream $S_{RDS2}$ and the portion $S_{RDS22}$ is only then separated from the bottoms stream $S_{RDS2}$ and subsequently $S_{RDS22}$ is recycled into $RD_2$.

(β-ii) at least one stream $S_{RDX2}$ distinct from $S_{RDB2}$ and $S_{RDS2}$ comprising ROH and water is discharged from $RD_1$. Energy is transferred from $S_{RDB1}$ to at least one, preferably precisely one, heat transfer medium $W_{ii1}$ distinct from $S_{RDX2}$, preferably via a heat exchanger WT, and then transferred from the at least one heat transfer medium $W_{ii1}$ to $S_{RDX2}$ and $S_{RDX2}$ is then recycled into $RD_2$.

It is preferable when $S_{RDX2}$ is withdrawn below the vapour stream $S_{RDB2}$ on $RD_2$. $S_{RDX2}$ is then especially selected from bottoms stream $S_{RDX2S}$, intermediate stream $S_{RDX2Z}$.

A bottoms stream $S_{RDX2S}$ is a stream whose withdrawal point on $RD_2$ is at the same height or below the withdrawal point of $S_{RDS2}$. $S_{RDX2S}$ may then be passed through a heat exchanger WT, in particular a bottoms evaporator VS, and energy transferred therein from $S_{RDB1}$ to $S_{RDX2S}$.

An intermediate stream $S_{RDX2Z}$ is a stream whose withdrawal point on $RD_2$ is between the withdrawal points of $S_{RDB2}$ and $S_{RDS2}$. $S_{RDX2Z}$ may then be discharged from $RD_2$ and passed through a heat exchanger WT, in particular an intermediate evaporator VZ, and energy transferred from $S_{RDB1}$ to $S_{RDX2Z}$ therein.

(β-iii) energy is transferred from $S_{RDB1}$ to at least one heat transfer medium $W_{iii1}$ distinct from $G_{RD2}$ and the at least one heat transfer medium $W_{iii1}$ is then passed through $RD_2$, thus transferring energy from the at least one heat transfer medium $W_{iii1}$ to $G_{RD2}$.

Such an embodiment may be realized for example when the at least one heat transfer medium $W_{iii1}$ is passed through the rectification column $RD_2$ through a conduit whose surface transfers energy from the at least one heat transfer medium $W_{iii1}$ to $G_{RD2}$ in $RD_2$.

Employable heat transfer media $W_1$ $W_2$, $W_3$, $W_4$, $W_5$/at least one heat exchanger $W_{i1}$/at least one heat exchanger $W_{ii1}$/at least one heat exchanger $W_{iii1}$ include any heat transfer media known to those skilled in the art. Such heat transfer media are preferably selected from the group consisting of: water; alcohol-water solutions; salt-water solutions, also including ionic liquids such as for example LiBr solutions, dialkylimidazolium salts such as especially dialkylimidazolium dialkylphosphates; mineral oils, for example diesel oils, thermal oils such as for example silicone oils; biological oils such as for example limonene; aromatic hydrocarbons such as for example dibenzyltoluene. The most preferred heat transfer medium is water.

Salt-water solutions that may be used are also described for example in DE 10 2005 028 451 A1 and WO 2006/134015 A1.

4.9 Addition or Fresh Alcohol

The alcohol ROH is consumed in the process according to the invention and especially in a continuous process mode therefore requires replacement with fresh alcohol ROH.

Fresh alcohol is in particular added to at least one of the columns selected from rectification column $RD_1$, rectification column RD$_2$, reactive rectification column RR$_A$ and if step (a2) is performed alternatively or in addition added to the reactive rectification column RR$_B$.

In a preferred embodiment of the present invention a stream S$_{XE1}$ distinct from S$_{AE1}$ and S$_{BE1}$ comprising ROH is accordingly added to at least one of the columns selected from rectification column RD$_1$, rectification column RD$_2$, reactive rectification column RR$_A$ and if step (a2) is performed alternatively or in addition added to reactive rectification column RR$_B$.

The introduction of the fresh alcohol ROH is effected, in particular, directly as reactant stream S$_{AE1}$ comprising ROH into the reaction column RR$_A$ or, in the embodiments in which step (a2) is carried out, into the reaction columns RR$_A$ and RR$_B$.

In the process according to the invention it is further preferable to employ the ROH-comprising vapour stream S$_{RDB1}$ at least partially as reactant stream S$_{AE1}$ in step (a1) and optionally as reactant stream S$_{BE1}$ in step (a2). The vapour stream S$_{RDB2}$ may alternatively or in addition be employed at least partially as reactant stream S$_{AE1}$ in step (a1) and optionally as reactant stream S$_{BE1}$ in step (a2).

In the particularly preferred embodiment in which S$_{RDB1}$ and S$_{RDB2}$ are employed at least partially as reactant stream S$_{AE1}$, in step (a1) and optionally as reactant stream S$_{BE1}$ in step (a2) S$_{RDB1}$ and S$_{RDB2}$ may be supplied to the respective reactive rectification column RR$_A$/RR$_B$ separately from one another or first mixed with one another and then supplied to the respective reactive rectification column RR$_A$/RR$_B$. S$_{RDB1}$ and S$_{RDB2}$ are preferably firstly mixed with one another and then supplied to the respective reactive rectification column RR$_A$/RR$_B$.

In this preferred embodiment it is yet more preferable when the fresh alcohol ROH is added to one of the rectification columns RD$_1$ and RD$_2$, preferably RD$_1$.

When the fresh alcohol ROH is added to the rectification column RD$_1$ or RD$_2$ it is preferably supplied either in the reinforcing section of the respective rectification column or directly at the top of the respective rectification column. The optimal feed point depends on the water content of the employed fresh alcohol and also on the desired residual water content in the vapour stream S$_{RDB1}$/S$_{RDB2}$. The higher the proportion of water in the employed alcohol and the higher the purity requirements of the vapour stream S$_{RDB1}$/S$_{RDB2}$ the more advantageous is a feed of a number of theoretical trays below the top of the rectification column RD$_1$/RD$_2$. Up to 20 theoretical trays below the top of the rectification column RD$_1$/RD$_2$ and in particular 1 to 5 theoretical trays are preferred.

When the fresh alcohol ROH is added to the rectification column RD$_1$/RD$_2$ it is added at the top of the rectification column RD$_1$/RD$_2$ at temperatures up to boiling point, preferably at room temperature. The fresh alcohol may have a dedicated feed provided for it or else when a portion of the alcohol withdrawn at the top of the rectification column RD$_1$/RD$_2$ is recycled may be mixed therewith after condensation and supplied to the rectification column RD$_1$/RD$_2$ together. In this case it is particularly preferable when the fresh alcohol is added to a condensate container in which the alcohol condensed from the vapour stream S$_{RDB1}$/S$_{RDB2}$ is collected.

FIGURES

FIG. 1

FIG. 1 shows a process according to the invention for producing alkali metal alkoxides with a corresponding interconnection of the rectification columns. Employed are a reactive rectification column ("reactive rectification column" is hereinbelow abbreviated to "reaction column") RR$_A$ <3A> at a pressure of p$_{3A}$ and two rectification columns RD$_1$ <1> and RD$_2$ <2> at pressures of p$_1$ and p$_2$ respectively. Here, p$_1$>p$_{3A}$>p$_2$.

In RR$_A$<3A> NaOH (stream S$_{AE2}$ <3A02>) is reacted with methanol (stream S$_{AE1}$ <3A01>) to afford a crude product RP$_A$ <3A07> comprising water, methanol, NaOH and sodium methoxide. At the lower end of RR$_A$<3A> a methanol-sodium methoxide mixture S$_{AP}$ <3A04> is withdrawn. The bottoms evaporator VS$_{3A}$ <3A06> at the lower end of the reaction column RR$_A$<3A> is used to adjust the concentration of the methoxide solution to the desired value in the resulting mixture S$_{AP*}$ <3A08>. There may additionally be attached at the bottom of the reaction column RR$_A$ <3A> a further evaporator, especially for startup of the reaction column RR$_A$ <3A> (not shown).

At the top of RR$_A$ <3A> a methanol-water mixture is withdrawn as vapour stream S$_{AB}$ <3A03>. S$_{AB}$ <3A03> is supplied to the first water/methanol column RD$_1$ <1>, wherein optionally S$_{AB}$ <3A03> is at the top of the reaction column RR$_A$ <3A> partially condensed in the condenser K$_{RRA}$ <3A05> and recycled in liquid form as reflux to the top of RR$_A$ <3A>. At least a portion of the vapour S$_{AB}$ <3A03> is then passed through a compressor VD$_{31}$ <10>, thus increasing the pressure of the vapour S$_{AB}$ <3A03> from p$_{3A}$ to the pressure p$_1$.

A methanol/water mixture G$_{RD1}$ <108> is thus obtained in the first rectification column RD$_1$ <1>. Methanol is distillative recovered as vapour S$_{RDB1}$ <101> in this first water/methanol column RD$_1$ <1>. The methanol recovered as vapour stream S$_{RDB1}$ <101> is at the withdrawal point <109> at the top of RD$_1$ <1> discharged therefrom and partially at the top of the rectification column RD$_1$ <1> condensed in the condenser K$_{RD1}$ <102> and recycled in liquid form as reflux to the top of RD$_1$ <1>. The remaining portion of the methanol recovered as vapour S$_{RDB1}$ <101> is for example via a throttle D$_{13}$ <11> decompressed to the pressure p$_3$ and introduced Into RR$_A$ <3A> as methanol stream S$_{AE1}$ <3A01>.

At the lower end (another term for "lower end of a rectification column" is "bottom of a rectification column") of RD$_1$ <1> a bottoms stream S$_{RDS1}$ <103> comprising water and methanol is discharged at the withdrawal point <110>. A first portion S$_{RDS11}$ <104> of the stream S$_{RDS1}$ <103> is supplied to a second water/methanol column RD$_2$ <2>, a second portion S$_{RDS12}$ <105> of the stream S$_{RDS1}$ <103> is via a bottoms evaporator recycled to VS$_{RD1}$ <106> in RD$_1$ <1>. S$_{RDS11}$ <104> is for example via a throttle D$_{12}$ <12> decompressed to the pressure p$_2$ before it is introduced Into RD$_2$ <2>.

A methanol/water mixture G$_{RD2}$ <206> is thus obtained in the second rectification column RD$_2$ <2>. In the rectification column RD$_2$ <2> residues of methanol from S$_{RDS11}$ <104> are separated from the water and distillatively recovered as vapour stream S$_{RDB2}$ <201> at the top of RD$_2$ <2>. The methanol recovered as vapour stream S$_{RDB2}$ <201> is at the withdrawal point <208> at the top of RD$_2$ <2> discharged therefrom and partially at the top of the rectification column RD$_2$ <2> condensed in the condenser K$_{RD2}$ <203> and recycled in liquid form as reflux to the top of RD$_2$ <2>. The remaining portion of the methanol recovered as vapour S$_{RDB2}$ <201> is passed through a compressor VD$_{23}$ <13>, thus compressed to the pressure p$_3$ and, together with the vapours $S_{RDB1}$ <101> from $RD_1$ <1> decompressed to the pressure $p_3$, introduced as methanol stream $S_{AE1}$ <3A01> into $RR_A$ <3A>.

At the lower end of $RD_2$ <2> a bottoms stream $S_{RDS2}$ <202> comprising water and optionally methanol is discharged at the withdrawal point <207>. A portion $S_{RDS22}$ <222> of $S_{RDS2}$ <202> is heated via a bottoms evaporator $VS_{RD2}$ <204> and recycled into $RD_2$ <2>.

For the heating of the portion of the bottoms stream $S_{RDS2}$ <202> which is recycled via $VS_{RD2}$ <204> into $RD_2$ <2> the energy liberated upon condensation of $S_{RDB1}$ <101> in the condenser $K_{RD1}$ <102> at the top of the rectification column $RD_1$ <1> is utilized. Said energy is recycled to $VS_{RD2}$ <204> as indicated by the dashed arrow <4>. The supply may be effected indirectly, i.e. using a heat transfer medium distinct from $S_{RDB1}$ <101> and $S_{RDS2}$ <202>, or else directly, i.e. through contacting of $S_{RDB1}$ <101> with $S_{RDS2}$ <202> in the condenser $K_{RD1}$ <102> or bottoms evaporator $VS_{RD2}$ <204>. In the case of direct contacting it is sufficient to employ only the condenser $K_{RD1}$ <102> and omit the bottoms evaporator $VS_{RD2}$ or to employ only the bottoms evaporator $VS_{RD2}$ <204> and omit the condenser $K_{RD1}$ <102> and then in each case pass both streams $S_{RDB1}$ <101> with $S_{RDS2}$ <202> through the condenser $K_{R1}$ <102> or the bottoms evaporator $VS_{RD2}$ <204> such that energy, preferably heat, is transferred from $S_{RDB1}$ <101> to $S_{RDS2}$ <202>.

FIG. 2

Figure 2:
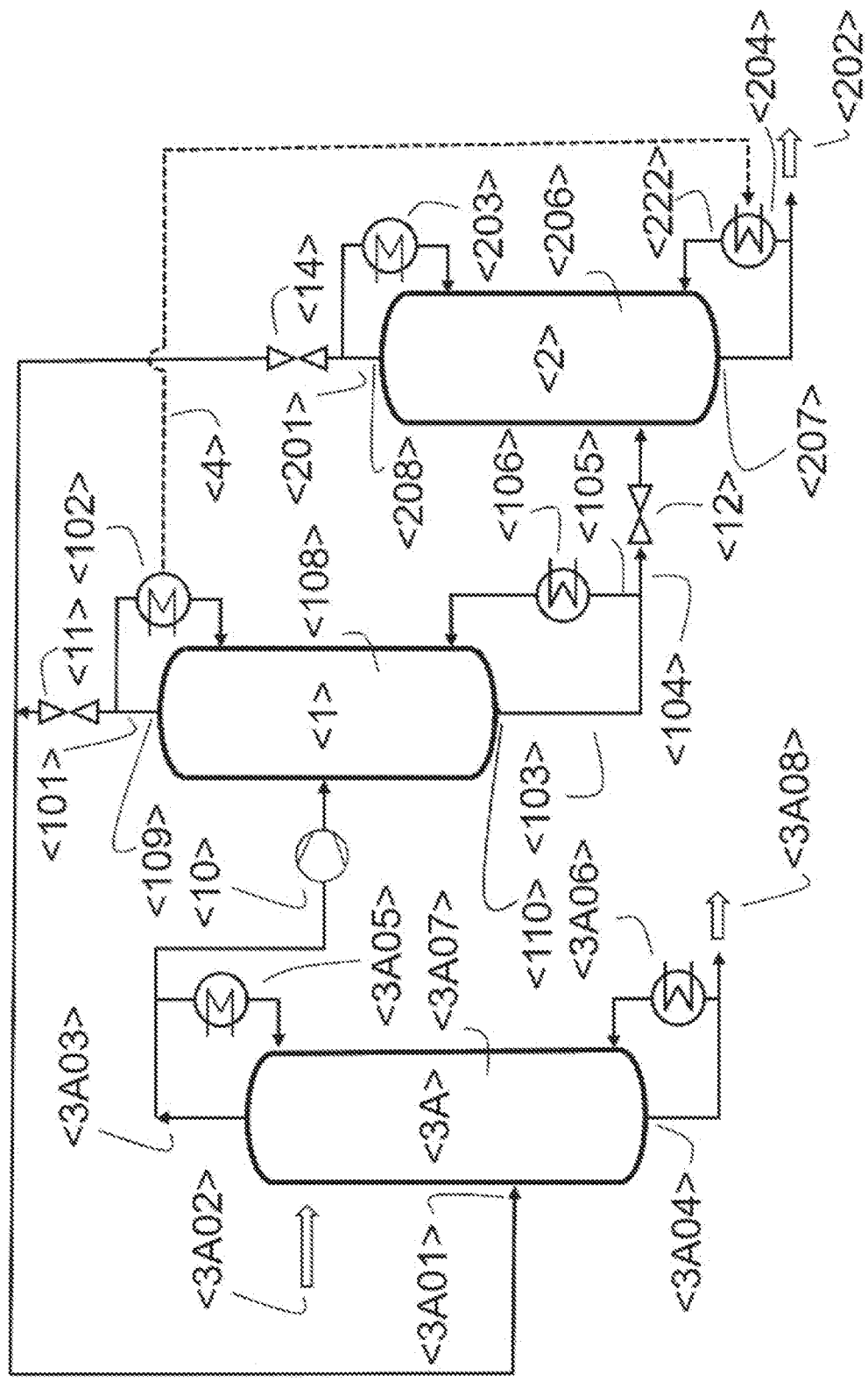
FIG. 2 shows a further process according to the invention for producing alkali metal alkoxides.

FIG. 2 shows a further process according to the invention for producing alkali metal alkoxides. This differs from the process shown in FIG. 1 in terms or the pressures in the respective columns. In the embodiment shown in FIG. 1 $p_1 > p_{3A} > p_2$ while in the embodiment shown in FIG. 2 $p_1 > p_2 > p_{3A}$. This different pressure regime makes the compressor $VD_{23}$ <13> unnecessary and a throttle $D_{23}$ <14> for example is attached. The throttle $D_{23}$ <14> decompresses the vapour stream $S_{RDB2}$ <201> from $p_2$ to the pressure $p_{3A}$ while in the embodiment according to FIG. 1 the compressor $VD_{23}$ <13> increases it from $p_2$ to the pressure $p_{3A}$.

FIG. 3

Figure 3:
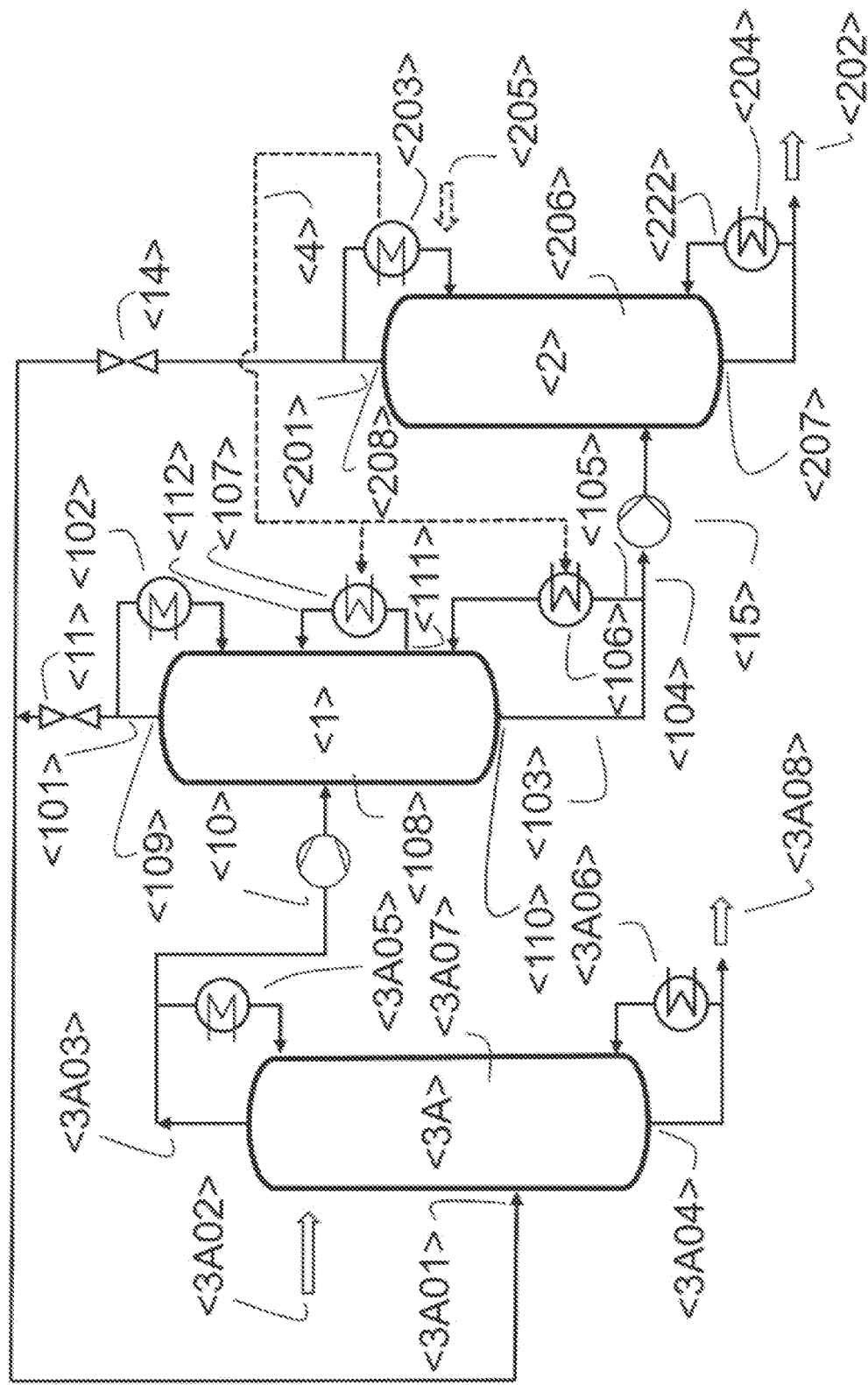
FIG. 3 shows one embodiment of a process not according to the invention for producing alkali metal alkoxides with a corresponding interconnection of the reactive rectification and rectification columns.

FIG. 3 shows one embodiment of a process not according to the invention for producing alkali metal alkoxides with a corresponding interconnection of the reactive rectification and rectification columns. Employed here, similarly to the embodiments described in FIGS. 1 and 2, are a reactive rectification column $RR_A$ <3A> at a pressure of $p_A$ and two rectification columns $RD_1$ <1> and $RD_2$ <2> having pressures of $p_1$ and $p_2$ respectively. Here, $p_2 > p_1 > p_{3A}$. The setup shown in FIG. 3 corresponds to the setup shown in FIG. 2 with the following exceptions:

1. Arranged at the rectification column $RD_1$ <1> next to the bottoms evaporator $VS_{RD1}$ <106> is an intermediate evaporator $VZ_{RD1}$ <107> which may be used to supply energy to the mixture $G_{RD1}$ <108> in $RD_1$ <1>. To this end the mixture $G_{RD1}$ <108> is at a withdrawal point <111> discharged from the rectification column $RD_1$ <1> as stream $S_{RDX1}$ <112>. $S_{RDX1}$ <112> is heated in $VZ_{RD1}$ <107> and recycled into the rectification column $RD_1$ <1>. A corresponding intermediate evaporator may also be attached to $RD_2$ <2> in the embodiments according to examples 1 and 2.

2. The throttle $D_{12}$ <12> is on account of the different pressures in the rectification columns $RD_1$ <1> and $RD_2$ <2> ($p_2 > p_1$) replaced by a pump P <15>. The reason for this difference is that the pressure of $S_{RDS11}$ <104>, when this stream is passed into $RD_2$ <2>, is according to the invention increased to $p_2$.

3. In an optional embodiment additional methanol as stream $S_{XE1}$ <205> is via the reflux at the rectification column $RD_2$ <2> added thereto.

4. The energy liberated upon condensation of the vapour $S_{RDB2}$ <201> at the top of $RD_2$ <2> is via the intermediate evaporator $VZ_{RD1}$ <107> transferred to $S_{RDX1}$ <112> and after reintroduction of $S_{RDX1}$ <112> into $RD_1$ <1> transferred from $S_{RDX1}$ <112> to the mixture $G_{RD1}$ <108> present in $RD_1$ <1>. Alternatively or in addition, energy liberated upon condensation of the vapour $S_{RDB2}$ <201> at the top of $RD_2$ <2> is via the bottoms evaporator $VS_{RD1}$ <106> transferred to the portion $S_{RDS12}$ <105> of the stream $S_{RDS1}$ <103>. Once $S_{RDS12}$ <105> is recycled into $RD_1$ <1> it transfers the energy to the mixture $G_{RD1}$ <108> present in $RD_1$ <1>. The energy flow is shown by the dashed arrow <4>.

In the case of direct contacting it is sufficient to employ only the condenser $K_{RD2}$ <203> and omit the bottoms evaporator $VS_{RD1}$ or to employ only the bottoms evaporator $VS_{RD1}$ <106> and omit the condenser $K_{RD2}$ <203> and then in each case pass both streams $S_{RDB2}$ <201> with $S_{RDS12}$ <105> through the condenser $K_{RD2}$ <203> or the bottoms evaporator $VS_{RD1}$ <106> such that energy, preferably heat, is transferred from $S_{RDS2}$ <201> to $S_{RDS12}$ <105>.

FIG. 4

Figure 4:
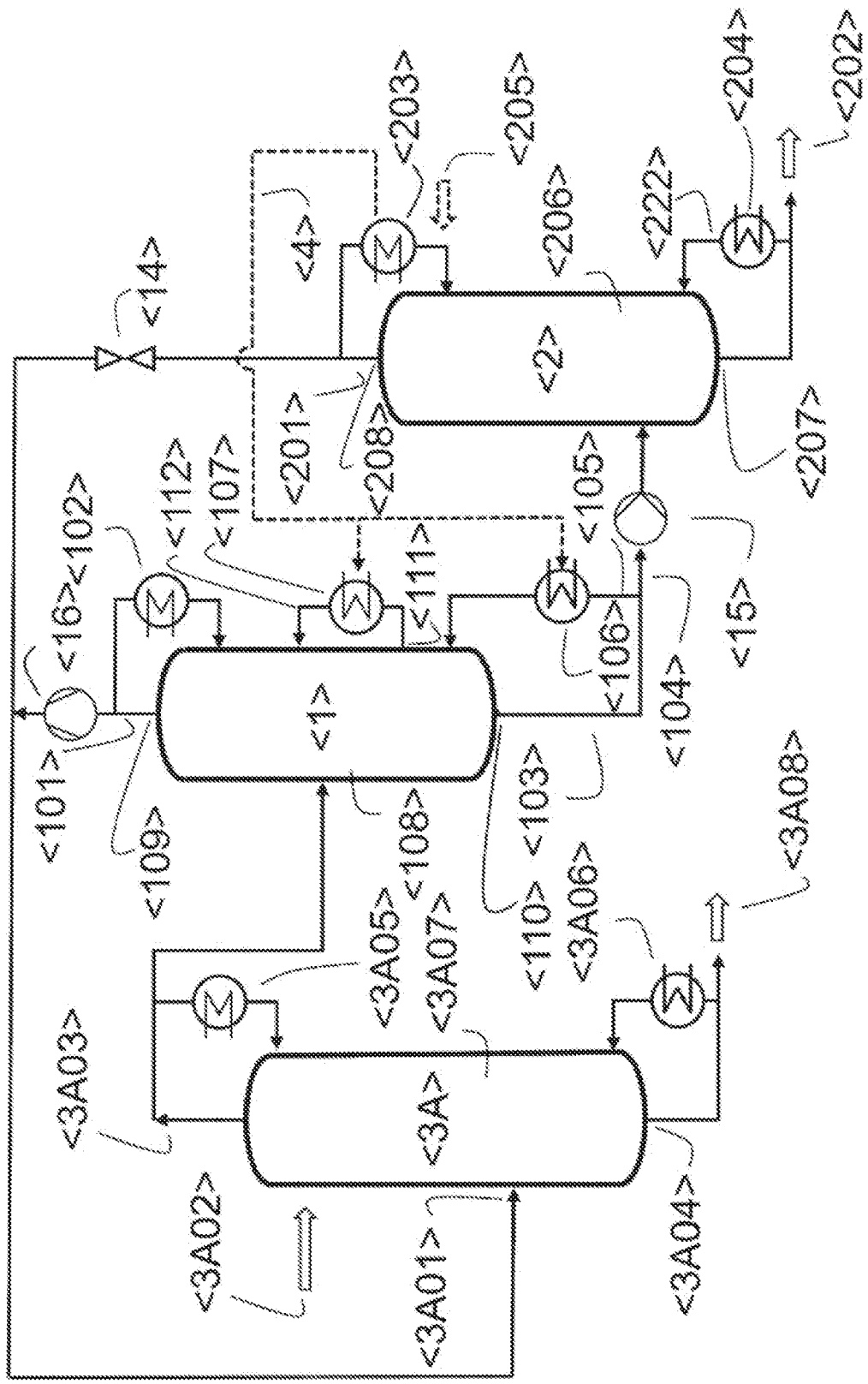
FIG. 4 shows a further embodiment of a process not according to the invention for producing alkali metal alkoxides with a corresponding interconnection of the rectification columns.

FIG. 4 shows a further embodiment of a process not according to the invention for producing alkali metal alkoxides with a corresponding interconnection of the rectification columns. Employed here, similarly to the embodiments described in FIGS. 1 and 2, are a reactive rectification column $RR_A$ <3A> at a pressure of $p_{3A}$ and two rectification columns $RD_1$ <1> and $RD_2$ <2> having pressures of $p_1$ and $p_2$ respectively. Here, $p_2 > p_{3A} > p_1$. The setup shown in FIG. 4 corresponds to the setup shown in FIG. 3 with the exception that the pressure $p_{3A} > p_1$. This allows the compressor $VD_{31}$ <10> to be omitted while the throttle $D_{13}$ <11> is replaced by the compressor $VD_{13}$ <16>.

5. EXAMPLES 5.1 Example 1 (Inventive)

The setup according to example 1 corresponds to the two-column interconnection according to FIG. 1, wherein $p_1 > p_{3A} > p_2$.

A stream $S_{AE2}$ <3A02> of aqueous NaOH (50% by weight) of 5 t/h is supplied to the top of a reaction column $RR_A$ <3A> at 25° C. A vaporous methanol stream $S_{AE1}$ <3A01> of 70.2 t/h is supplied in countercurrent above the bottom of the reaction column $RR_A$ <3A>. The reaction column $RR_A$ <3A> is operated at a pressure $p_{3A}$ of 1.6 bar. At the bottom of the column $RR_A$ <3A> a virtually water-free product stream $S_{AP*}$ <3A08> of 10.8 t/h is withdrawn (30% by weight sodium methoxide in methanol). At the evaporator $VS_{3A}$ <3A06> of the reaction column $RR_A$ <3A> about 0.7 MW of heating power are introduced using heating steam. A vaporous methanol-water stream $S_{AB}$ <3A03> is withdrawn at the top of the reaction column $RR_A$ <3A>. A portion of this stream is via a condenser $K_{RRA}$ <3A05> recycled to the reaction column $RR_A$ <3A> and the remaining portion (64.4 t/h) compressed in a compressor $VD_{31}$ <10> to 7.1 bar, wherein about 4 MW of compressor power are necessary, and supplied to a first rectification column $RD_1$ <1>. The rectification column $RD_1$ <1> is operated at $p_1 = \sim 7$ bar. At the top of the rectification column $RD_1$ <1> a liquid fresh methanol stream of 9.5 t/h is supplied (not shown in FIG. 1) and vaporous methanol stream $S_{RDB1}$ <101> is withdrawn. A portion of $S_{RDB1}$ <101> is via the condenser $K_{RD1}$ <102> recycled into column $RD_1$ <1>. The remaining portion of SRDS <101> (42.9 t/h) is suppled to the reaction column $RR_A$ <3A>. Condenser $K_{RD1}$ <102> of column $RD_1$ <1> which is simultaneously the evaporator $VS_{RD2}$ of the second rectification column $RD_2$ <2> provides the heating power for the column $RD_2$ <2>. The embodiment according to example 1 utilized direct contacting where the condenser $K_{RD1}$ <102> is simultaneously employed as bottoms evaporator $VS_{RD2}$ <204>.

Discharged at the bottom of the rectification column $RD_1$ <1> is a liquid stream of a water-methanol mixture $S_{RDS1}$ <103> of which a portion $S_{RDS12}$ <104> of 30.9 t/h is passed into the rectification column $RD_2$ <2> and the remaining portion of the stream SROS <103> is recycled as $S_{RDS11}$ <105> into $RD_1$ <1>. At the evaporator $VS_{RD1}$ <106> of the rectification column $RD_1$ <1> about 5.4 MW of heating power are introduced via heating steam.

The rectification column $RD_2$ <2> is operated at a pressure $p_2$ of 1.1 bar. Withdrawn at the top of the rectification column $RD_2$ <2> is a vaporous methanol stream $S_{RDB2}$ <201>. A portion of $S_{RDB2}$ <201> is via the condenser $K_{RD2}$ <203> recycled into column $RD_2$ <2>. The remaining portion of $S_{RDB2}$ <201> (27.3 t/h) is supplied to the reaction column $RR_A$ <3A>. This portion of the vaporous stream $S_{RDB2}$ <201> is compressed to 2 bar in a compressor $VD_{23}$ <13>, wherein about 0.6 MW of compressor power are necessary. Discharged at the bottom of the rectification column $RD_2$ <2> is a liquid stream of water $S_{RDS2}$ <202> (contaminated with 500 ppmw of methanol) of 3.7 t/h. For evaporation at the rectification column $RD_2$ <2> (since direct heat integration is effected the function of the bottoms evaporator $VS_{RD2}$ <204> shown in FIG. 1 is co-assumed by the condenser $K_{RD1}$ <102>) about 14.8 MW of heating power are introduced to a portion $S_{RDS22}$ <222> of $S_{RDS2}$ <202> via heat integration with the column $RD_1$ <1>.

The respective, non-recycled portions of the vaporous methanol streams $S_{RDB1}$ <101> and $S_{RDB2}$ <201> withdrawn at the tops of $RD_1$ <1> and $RD_2$ <2> are mixed and recycled to the bottom of reaction column $RR_A$ <3A>.

Altogether in this example about 6.1 MW of heating power via heating steam and about 4.6 MW of electrical power (compressor power) are required and must be externally provided.

5.2 Example 2 (inventive)

The setup according to example 2 corresponds to the two-column interconnection according to FIG. 2, wherein $p_1 > p_2 > p_{3A}$.

A stream $S_{AE2}$ <3A02> of aqueous NaOH (50% by weight) of 5 t/h is supplied to the top of a reaction column $RR_A$ <3A> at 25° C. A vaporous methanol stream $S_{AE1}$ <3A01> of 70.2 t/h is supplied in countercurrent above the bottom of the reaction column $RR_A$ <3A>.

The reaction column $RR_A$ <3A> is operated at a pressure $p_{3A}$ of 1.1 bar. At the bottom of the column $RR_A$ <3A> a virtually water-free product stream $S_{AP*}$ <3A08> of 10.8 t/h is withdrawn (30% by weight sodium methoxide in methanol). At the evaporator $VS_{3A}$ <3A06> of the reaction column $RR_A$<3A> about 2.4 MW of heating power are introduced using heating steam. A vaporous methanol-water stream $S_{AB}$ <3A03> is withdrawn at the top of the reaction column $RR_A$ <3A>. A portion of this stream is via a condenser $K_{RRA}$ <3A05> recycled to the reaction column $RR_A$ <3A> and the remaining portion (64.4 t/h) compressed in a compressor $VD_{31}$ <10> to 9 bar, wherein about 5.8 MW of compressor power are necessary, and supplied to a first rectification column $RD_1$ <1>. The rectification column $RD_1$ <1> is operated at $p_1$=~8.9 bar. At the top of the rectification column $RD_1$ <1> a liquid fresh methanol stream of 9.5 t/h is supplied (not shown in FIG. 2) and vaporous methanol stream $S_{RDB1}$ <101> is withdrawn. A portion of $S_{RDB1}$ <101> is via the condenser $K_{RD1}$ <102> recycled into column $RD_1$ <1>. The remaining portion of $S_{RDB1}$ <101> (42.9 t/h) is supplied to the reaction column $RR_A$ <3A>. Condenser $K_{RD1}$ <102> of column $RD_1$ <1> which is simultaneously the evaporator $VS_{RD2}$ <204> of the second rectification column $RD_2$ <2> provides the heating power for the column $RD_{3<2>}$. The embodiment according to example 2 utilized direct contacting where the condenser $K_{RD1}$ <102> is simultaneously employed as bottoms evaporator $VS_{RD2}$ <204>.

Discharged at the bottom of the rectification column $RD_1$ <1> is a liquid stream of a water-methanol mixture $S_{RDS1}$ <103> of which a portion $S_{RDS12}$ <104> of 31.9 t/h is passed into the rectification column $RD_2$ <2> and the remaining portion of the stream $S_{RDS1}$ <103> is recycled as $S_{RDS11}$ <105> Into $RD_1$ <1>. At the evaporator $VS_{RD1}$ <106> of the rectification column $RD_1$ <1> about 5.2 MW of heating power are introduced via heating steam.

The rectification column $RD_2$ <2> is operated at a pressure $p_2$ of 1.5 bar. Withdrawn at the top of the rectification column $RD_2$ <2> is a vaporous methanol stream $S_{RDB2}$ <201>. A portion of $S_{RDB2}$ <201> is via the condenser $K_{RD2}$ <203> recycled into column $RD_2$ <2>. The remaining portion of $S_{RDB2}$ <201> (28.2 t/h) is supplied to the reaction column $RR_A$ <3A>. Discharged at the bottom of the rectification column $RD_2$ <2> is a liquid stream of water $S_{RDS2}$ <202> (contaminated with 500 ppmw of methanol) of 3.7 t/h. For evaporation at the rectification column $RD_2$ <2> (since direct heat integration is effected the function of the bottoms evaporator $VS_{RD2}$ <204> shown in FIG. 1 is co-assumed by the condenser $K_{RD1}$ <102>) about 15.9 MW of heating power are introduced to a portion $S_{RDS22}$ <222> of $S_{RDS2}$ <202> via heat integration with the column $RD_1$ <1>. The respective, non-recycled portions of the vaporous methanol streams $S_{RDB1}$ <101> and $S_{RDB2}$ <201> withdrawn at the tops of $RD_1$ <1> and $RD_1$ <2> are mixed and recycled to the bottom of reaction column $RR_A$ <3A>.

Altogether in this example about 7.6 MW of heating power via heating steam and about 5.8 MW of electrical power (compressor power) are required and must be externally provided.

5.3 Example 3 (Noninventive)

The setup according to example 3 corresponds to the two-column interconnection according to FIG. 3, wherein $p_2 > p_1 > p_{3A}$. The intermediate evaporator $VZ_{RD1}$ <107> with the stream $S_{RDX1}$ <112> withdrawn at the withdrawal point <111> shown in FIG. 3 is likewise omitted in the setup according to example 3. The condenser $K_{RD2}$ <203> is also simultaneously the bottoms evaporator $VS_{RD1}$ <106>. The fresh methanol stream $S_{XE1}$ <205> is in FIG. 3 supplied to the rectification column $RD_2$ <2> but in the setup according to example 3 supplied to $RD_1$ <1>.

A stream $S_{AE2}$ <3A02> of aqueous NaOH (50% by weight) of 5 t/h is supplied to the top of a reaction column $RR_A$ <3A> at 25° C. A vaporous methanol stream $S_{AE1}$ <3A01> of 70.2 t/h is supplied in countercurrent above the bottom of the reaction column $RR_A$ <3A>. The reaction column $RR_A$ <3A> is operated at a pressure $p_{3A}$ of 1.1 bar. At the bottom of the column $RR_A$ <3A> a virtually water-free product stream $S_{AP*}$ <3A08> of 10.8 t/h is withdrawn (30% by weight sodium methoxide in methanol). At the evaporator $VS_{3A}$ <3A06> of the reaction column $RR_A$ <3A> about 1.4 MW of heating power are introduced using heating steam. A vaporous methanol-water stream $S_{AB}$ <3A03> is withdrawn at the top of the reaction column $RR_A$ <3A>. A portion of this stream is via a condenser $K_{RRA}$ <3A05> recycled to the reaction column $RR_A$ <3A> and the remaining portion (64.4 t/h) compressed in a compressor $VD_{31}$ <10> to 1.7 bar, wherein about 1.1 MW of compressor power are necessary, and supplied to a first rectification column $RD_1$ <1>. The rectification column $RD_1$ <1> is operated at $p_1$=~1.5 bar. At the top of the rectification column $RD_1$ <1> a liquid fresh methanol stream $S_{XE1}$ <205> of 9.5 t/h is supplied (shown at the top of the rectification column $RD_2$ <2> in FIG. 3) and vaporous methanol stream $S_{RDB1}$ <101> is withdrawn. A portion of $S_{RDB1}$ <101> is via the condenser $K_{RD1}$ <102> recycled into column $RD_1$ <1>. The remaining portion of $S_{RDB1}$ <101> (58.8 t/h) is supplied to the reaction column $RR_A$ <3A>. The embodiment according to example 3 utilized direct contacting where the condenser $K_{RD2}$ <203> simultaneously serves as bottoms evaporator $VS_{RD1}$ <106>.

Discharged at the bottom of the rectification column $RD_1$ <1> is a liquid stream of a water-methanol mixture $S_{RDS1}$ <103> of which a portion $S_{RDS12}$ <104> or 17 t/h is passed into the rectification column $RD_2$ <2> and the remaining portion of the stream $S_{RDS1}$ <103> is recycled as $S_{RDS11}$ <105> into $RD_1$ <1>.

The pressure of the discharged stream $S_{RDS12}$ <104> is in a pump P <15> increased to 9 bar and the stream $S_{RDS12}$ <104> supplied to the second rectification column $RD_2$ <2>. The rectification column $RD_2$ <2> is operated at a pressure $p_2$ of 8.9 bar. In the condenser $K_{RD2}$ <203> of column $RD_2$ <2> which is simultaneously the evaporator of the column $RD_1$ <1> about 8.2 MW of heating power are provided for the column $RD_1$ <1>. Withdrawn at the top of the rectification column $RD_2$ <2> is a vaporous methanol stream $S_{RDB2}$ <201>. A portion of $S_{RDB2}$ <201> is via the condenser $K_{RD2}$ <203> recycled into column $RD_2$ <2>. The remaining portion of $S_{RDB2}$ <201> (13.4 t/h) is supplied to the reaction column $RR_A$ <3A>. Discharged at the bottom of the rectification column $RD_2$ <2> is a liquid stream of water (contaminated with 500 ppmw of methanol) of 3.7 t/h. At the evaporator $VS_{RD2}$ <204> of the rectification column $RD_2$ <2> about 12.9 MW of heating power are introduced using heating steam.

The respective, non-recycled portions of the vaporous methanol streams $S_{RDB1}$ <101> and $S_{RDB2}$ <201> withdrawn at the tops of $RD_1$ <1> and $RD_2$ <2> are mixed, decompressed and recycled to the bottom of reaction column $RR_A$ <3A>.

Altogether in this example about 14.3 MW of heating power via heating steam and about 1.1 MW of electrical power (compressor power) are required and must be externally provided.

5.4 Example 4 (Noninventive)

The setup according to example 4 corresponds to the two-column interconnection according to FIG. 4, wherein $p_2$>$p_{3A}$>$p_1$. The intermediate evaporator $VZ_{RD1}$ <107> with the stream $S_{RDX1}$ <112> withdrawn at the withdrawal point <111> shown in FIG. 4 is likewise omitted in the setup according to example 4. The condenser $K_{RD2}$ <203> is also simultaneously the bottoms evaporator $VS_{RD1}$ <106>. The fresh methanol stream $S_{XE1}$ <205> is in FIG. 4 supplied to the rectification column $RD_2$ <2> but in the setup according to example 4 supplied to $RD_1$ <1>.

A stream $S_{AE2}$ <3A02> of aqueous NaOH (50% by weight) of 5 t/h is supplied to the top of a reaction column $RR_A$ <3A> at 25° C. A vaporous methanol stream $S_{AE1}$ <3A01> of 70.2 t/h is supplied in countercurrent above the bottom of the reaction column $RR_A$ <3A>. The reaction column $RR_A$ <3A> is operated at a pressure $p_{3A}$ of 1.8 bar. At the bottom of the column $RR_A$ <3A> a virtually water-free product stream $S_{AP*}$ <3A08> of 10.8 t/h is withdrawn (30% by weight sodium methoxide in methanol). At the evaporator $VS_{3A}$ <3A06> of the reaction column $RR_A$ <3A> about 0.8 MW of heating power are introduced using heating steam. A vaporous methanol-water stream $S_{AB}$ <3A03> is withdrawn at the top of the reaction column $RR_A$ <3A>. A portion of this stream is via a condenser $K_{RRA}$ <3A05> recycled to the reaction column $RR_A$ <3A> and the remaining portion (64.4 t/h) is supplied to a first rectification column $RD_1$ <1>. The rectification column $RD_1$ <1> is operated at $p_1$=~1.1 bar. At the top of the rectification column $RD_1$ <1> a liquid fresh methanol stream $S_{XE1}$ <205> of 9.5 t/h is supplied (shown at the top of the rectification column $RD_2$ <2> in FIG. 4) and vaporous methanol stream $S_{RDB1}$ <101> is withdrawn.

A portion of $S_{RDB1}$ <101> is via the condenser $K_{RD1}$ <102> recycled into column $RD_1$ <1>. The remaining portion of $S_{RDB1}$ <101> (55 t/h) is compressed to 2 bar in a compressor $VD_{13}$ <16>, wherein about 1.2 MW of compressor power are required, and supplied to the reaction column $RR_A$ <3A>. Discharged at the bottom of the rectification column $RD_1$ <1> is a liquid stream of a water-methanol mixture $S_{RDS1}$ <103> of which a portion $S_{RDS12}$ <104> of 18.9 t/h is passed into the rectification column $RD_2$ <2> and the remaining portion of the stream $S_{RDS1}$ <103> is recycled as $S_{RDS11}$ <105> into $RD_1$ <1>.

The pressure or the discharged stream $S_{RDS12}$ <104> is in a pump P <15> increased to 3.4 bar and the stream supplied to the second rectification column $RD_2$ <2>. The rectification column $RD_2$ <2> is operated at a pressure $p_2$ of 3.2 bar. In the condenser $K_{RD2}$ <203> of column $RD_2$ <2> which is simultaneously the evaporator of the column $RD_1$ <1>, about 6.3 MW of heating power are provided for the column $RD_1$ <1>. Withdrawn at the top of the rectification column $RD_2$ <2> is a vaporous methanol stream $S_{RDB2}$ <201>. A portion of $S_{RDB2}$ <201> is via the condenser $K_{RD2}$ <203> recycled into column $RD_2$ <2>. The remaining portion of $S_{RDB2}$ <201> (15.2 t/h) is supplied to the reaction column $RR_A$ <3A>. Discharged at the bottom of the rectification column $RD_2$ <2> is a liquid stream of water (contaminated with 500 ppmw of methanol) of 3.7 t/h. At the evaporator $VS_{RD2}$ <204> or the rectification column $RD_2$ <2> about 11.4 MW of heating power are introduced using heating steam.

The respective, non-recycled portions of the vaporous methanol streams $S_{RDB1}$ <101> and $S_{RDB2}$ <201> withdrawn at the tops of $RD_1$ <1> and $RD_2$ <2> are mixed and recycled to the bottom of reaction column $RR_A$ <3A>.

Altogether in this example about 12.2 MW of heating power via heating steam and about 1.2 MW of electrical power (compressor power) are required and must be externally provided.

5.5 Result

Comparison of the proportion of heating steam and electrical current required to cover the energy demand in the inventive and noninventive examples reveals that the inventive process surprisingly makes it possible to cover a large proportion of the energy demand through electrical energy and to minimize the proportion of the power to be provided through heating steam.

The invention claimed is:

1. A process for producing at least one alkali metal alkoxide of formula $M_AOR$, wherein R is a $C_1$ to $C_6$ hydrocarbon radical and wherein $M_A$ is sodium or potassium, the process comprising:
   (a1) reacting a reactant stream $S_{AE1}$ comprising ROH with a reactant stream $S_{AE2}$ comprising $M_AOH$, in countercurrent at a pressure $p_{3A}$ and a temperature $T_{3A}$ in a first reactive rectification column $RR_A$, to afford a crude product $RP_A$ comprising $M_AOR$, water, the ROH, and the $M_AOH$, wherein R is a $C_1$ to $C_6$ hydrocarbon radical and $M_A$ is sodium or potassium, and
   withdrawing a bottoms product stream $S_{AP}$ comprising the ROH and the $M_AOR$ at a lower end of the first reactive rectification column $RR_A$, and withdrawing a vapour stream $S_{AB}$ comprising the water and the ROH at an upper end of the first reactive rectification column $RR_A$, and
   (a2) optionally, simultaneously with and spatially separate from (a1), reacting a reactant stream $S_{BE1}$ comprising ROH with a reactant stream $S_{BE2}$ comprising $M_BOH$, in countercurrent at a pressure $p_{3B}$ and a temperature $T_{3B}$ in a second reactive rectification column $RR_B$, to afford a crude product $RP_B$ comprising $M_BOR$, water, the ROH, and the $M_BOH$, wherein $M_B$ is sodium or potassium, and
   withdrawing a bottoms product stream $S_{BP}$ comprising the ROH and the $M_BOR$ at a lower end of the second reactive rectification column $RR_B$, and withdrawing a vapour stream $S_{BB}$ comprising the water and the ROH at an upper end of the second reactive rectification column $RR_B$,
   (b) passing the vapour stream $S_{AB}$ into a first rectification column $RD_1$, and if (a2) is performed, the vapour stream $S_{BB}$ is also passed into the first rectification column $RD_1$ in admixture with the vapour stream $S_{AB}$ or separately from the vapour stream $S_{AB}$, to obtain a mixture $G_{RD1}$ comprising water and ROH in the first rectification column $RD_1$,
   (c) separating the mixture $G_{RD1}$ in the first rectification column $RD_1$ at a pressure $p_1$ and a temperature $T_1$, into an ROH-comprising vapour stream $S_{RDB1}$ at an upper end of the first rectification column $RD_1$, and a bottoms stream $S_{RDS1}$ comprising water and ROH at a lower end of the first rectification column $RD_1$,
   (d) passing the bottoms stream $S_{RDS1}$ completely or partially into a second rectification column $RD_2$, to obtain a mixture $G_{RD2}$ comprising water and ROH in the second rectification column $RD_2$,
   (e) separating the mixture $G_{RD2}$ at a pressure $p_2$ and a temperature $T_2$ into an ROH-comprising vapour stream $S_{RDB2}$ at a top of the second rectification column $RD_2$, and a bottoms stream $S_{RDS2}$ comprising water at a lower end of the second rectification column $RD_2$, and
   (f) transferring energy from the vapour stream $S_{RDB1}$ to the mixture $G_{RD2}$ in the second rectification column $RD_2$,
   wherein $p_1 > p_2$, $p_1 > p_{3A}$, and wherein if (a2) is performed, $p_1 > p_{3B}$.

2. The process according to claim 1, wherein in (f), energy is directly transferred from the vapour stream $S_{RDB1}$ to the mixture $G_{RD2}$.

3. The process according to claim 2, wherein at least one of (α-i), (α-ii), and/or (α-iii) is performed:
   (α-i) energy from the vapour stream $S_{RDB1}$ is transferred to a portion $S_{RDS22}$ of the bottoms stream $S_{RDS2}$ discharged from the second rectification column $RD_2$, and the portion $S_{RDS22}$ is then recycled into the second rectification column $RD_2$;
   (α-ii) at least one stream $S_{RDX2}$, distinct from the vapour stream $S_{RDB2}$ and the bottoms stream $S_{RDS2}$, comprising ROH and water is discharged from the second rectification column $RD_2$, and energy is then transferred from the vapour stream $S_{RDB1}$ to the at least one stream $S_{RDX2}$, and the at least one stream $S_{RDX2}$ is recycled into the second rectification column $RD_2$; and/or
   (α-iii) the vapour stream $S_{RDB1}$ is passed through the second rectification column $RD_2$, thus transferring energy from the vapour stream $S_{RDB1}$ to the mixture $G_{RD2}$.

4. The process according to claim 3, wherein the at least one stream $S_{RDX2}$ is withdrawn below the vapour stream $S_{RDB2}$ on the second rectification column $RD_2$.

5. The process according to claim 1, wherein in (f), energy is indirectly transferred from the vapour stream $S_{RDB1}$ to the mixture $G_{RD2}$.

6. The process according to claim 5, wherein at least one of (β-i), (β-ii), and/or (β-iii) is performed:
   (β-i) a portion $S_{RDS22}$ of the bottoms stream $S_{RDS2}$ discharged from the second rectification column $RD_2$ is recycled into the second rectification column $RD_1$, wherein energy is transferred from the vapour stream $S_{RDB1}$ to at least one heat transfer medium $W_{i1}$, distinct from the portion $S_{RDS22}$, and then transferred from the at least one heat transfer medium $W_{i1}$ to the portion $S_{RDS22}$, and the portion $S_{RDS22}$ is then recycled into the second rectification column $RD_2$;
   (β-ii) at least one stream $S_{RDX2}$, distinct from the vapour stream $S_{RDB2}$ and the bottoms stream $S_{RDS2}$, comprising ROH and water is discharged from the second rectification column $RD_2$, and energy is transferred from the vapour stream $S_{RDB1}$ to at least one heat transfer medium $W_{ii1}$, distinct from the at least one stream $S_{RDX2}$, and then transferred from the at least one heat transfer medium $W_{ii1}$ to the at least one stream $S_{RDX2}$, and the at least one stream $S_{RDX2}$ is then recycled into the second rectification column $RD_2$; and/or
   (β-iii) energy is transferred from the vapour stream $S_{RDB1}$ to at least one heat transfer medium $W_{iii1}$, distinct from the mixture $G_{RD2}$, and the at least one heat transfer medium $W_{iii1}$ is then passed through the second rectification column $RD_2$, thus transferring energy from the at least one heat transfer medium $W_{iii1}$ to the mixture $G_{RD2}$.

7. The process according to claim 6, wherein each of the at least one heat transfer medium $W_{i1}$, the at least one heat transfer medium $W_{ii1}$, and the at least one heat transfer medium $W_{iii1}$ is water.

8. The process according to claim 6, wherein the at least one stream $S_{RDX2}$ is withdrawn below the vapour stream $S_{RDB2}$ on the second rectification column $RD_2$.

9. The process according to claim 1, wherein the vapour stream $S_{RDB2}$ is at least partially employed as the reactant stream $S_{AE1}$ in the first reactive rectification column $RR_A$, and if (a2) is performed, the vapour stream $S_{RDB2}$ is alternatively or in addition employed as the reactant stream $S_{BE1}$ in the second reactive rectification column $RR_B$.

10. The process according to claim 1, wherein the vapour stream $S_{RDB1}$ is at least partially employed as the reactant stream $S_{AE1}$ in the first reactive rectification column $RR_A$, and if (a2) is performed, the vapour stream $S_{RDB1}$ is alternatively or in addition employed as the reactant stream $S_{BE1}$ in the second reactive rectification column $RR_B$.

11. The process according to claim 1, wherein a stream $S_{XE1}$, distinct from the reactant stream $S_{AE1}$ and the reactant stream $S_{BE1}$, comprising ROH is added to at least one of the columns selected from the group consisting of the first rectification column $RD_1$, the second rectification column $RD_2$, and the first reactive rectification column $RR_A$, and if (a2) is performed, the stream $S_{XE1}$ is alternatively or in addition added to the second reactive rectification column $RR_a$.

12. The process according to claim 1, wherein R is methyl or ethyl.

13. The process according to claim 1, wherein (a2) is performed.

14. The process according to claim 1, wherein $p_{3A} > p_2$, and wherein if (a2) is performed, $p_{3B} > p_2$.

15. The process according to claim 1, wherein the bottoms stream $S_{RDS2}$ comprises water and ROH.

16. The process according to claim 1, wherein the process is carried out continuously.

* * * * *

UNITED STATES PATENT AND TRADEMARK OFFICE
CERTIFICATE OF CORRECTION

PATENT NO. : 11,661,388 B2
APPLICATION NO. : 17/659053
DATED : May 30, 2023
INVENTOR(S) : Dirk Roettger et al.

It is certified that error appears in the above-identified patent and that said Letters Patent is hereby corrected as shown below:

In the Claims

Column 31, Line 25, Claim 1, currently reads, "comprising $M_B$ OR, water," and should read --comprising $M_B$OR, water--;

Column 32, Line 26, Claim 6, currently reads, "second rectification column $RD_1$," and should read --second rectification column $RD_2$,--; and Column 33, Line 11, Claim 11, currently reads, "$RR_a$." and should read --$RR_B$.--.

Signed and Sealed this
Twenty-ninth Day of August, 2023

Katherine Kelly Vidal
*Director of the United States Patent and Trademark Office*